US011841366B2

(12) United States Patent
Cummings et al.

(10) Patent No.: US 11,841,366 B2
(45) Date of Patent: *Dec. 12, 2023

(54) COMPOSITIONS AND METHODS FOR DETECTION OF WILD TYPE CRY PROTEIN AND A HYBRID CRY PROTEIN

(71) Applicant: Syngenta Participations AG, Basel (CH)

(72) Inventors: Simone Cummings, Research Triangle Park, NC (US); Julie Smith, Research Triangle Park, NC (US); Magda Foege, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 778 days.

This patent is subject to a terminal disclaimer.

(21) Appl. No.: 16/821,170

(22) Filed: Mar. 17, 2020

(65) Prior Publication Data
US 2021/0293807 A1    Sep. 23, 2021

Related U.S. Application Data

(62) Division of application No. 15/755,721, filed as application No. PCT/US2016/048580 on Aug. 25, 2016, now Pat. No. 10,634,675.

(60) Provisional application No. 62/215,982, filed on Sep. 9, 2015.

(51) Int. Cl.
*G01N 33/543* (2006.01)
*G01N 33/577* (2006.01)
*C07K 16/12* (2006.01)
*G01N 33/58* (2006.01)

(52) U.S. Cl.
CPC ... *G01N 33/54393* (2013.01); *C07K 16/1278* (2013.01); *G01N 33/577* (2013.01); *G01N 33/581* (2013.01); *G01N 2333/325* (2013.01)

(58) Field of Classification Search
None
See application file for complete search history.

(56) References Cited

U.S. PATENT DOCUMENTS

| 8,344,207 B2 | 1/2013 | Bogdanova et al. |
| 10,634,675 B2 * | 4/2020 | Cummings ............ G01N 33/68 |
| 2003/0208790 A1 | 11/2003 | Jansens et al. |

FOREIGN PATENT DOCUMENTS

| CN | 2012100124984 A | 7/2012 |
| WO | 2001/45122 A1 | 6/2001 |

OTHER PUBLICATIONS

"Development and Validation of a Sensitive Enzyme Immunoassay for Surveillance of Cry1Ab Toxin in Bovine Blood Plasma of Cows Fed Bt- maize (MON810)", Analytica Chimica Acta, Nov. 19, 2007, vol. 607, pp. 106-113, abstract; p. 107, second column, fifth paragraph, DOI: 10.1016/j.aca.2007.11.022.
International Search Report in application No. PCT/US16/48580 filed Aug. 25, 2016, dated Nov. 29, 2016, (12 pages).
Extended European Search Report for EP Application No. 16844883.5 dated Jan. 15, 2019, (8 pages).
Houghten et al., Vaccines, 1986, Edited by Fred Brown: Cold Spring Harbor Laboratory, 1986.

* cited by examiner

*Primary Examiner* — Ellen J Marcsisin
(74) *Attorney, Agent, or Firm* — Katherine Seguin

(57) ABSTRACT

The invention relates generally to immunoassays, and more particularly to monoclonal antibodies and immunoassays for the differential detection and quantitation of a wild-type crystal protein, such as a wild-type-Cry1Ab, from *Bacillus thuringiensis* and hybrid crystal proteins, which comprise all or a significant portion of the wild-type Cry protein in complex biological samples comprising both the wild-type Cry protein and one or more of the hybrid Cry proteins.

16 Claims, 10 Drawing Sheets
Specification includes a Sequence Listing.

```
Cry1Ab     1   MDNNPNINECI---PYNCLSNPEVEVLGGERIETGYTPIDISLSLTQFLLSEFVPGAGFV
eCry3.1Ab  1   --MTS.GRQ.AGIR..D-------.RQQHR.----LDS.T.KDVIQKISVV.DL

Cry1Ab     58  LGLVDIIWG--------IFGPSQ--WDAFLVQIEQLINQRIEEFARNQAISRLEGL
eCry3.1Ab  43  ..V.GFPF.GALVSFYTNFLNTIW..EDP.K..ME.V.A.MD.K.ADY.K.K.LAE.Q..

Cry1Ab     104 SNLYQIYAESFREWEADPT---NPALREEMRIQFNDMNSALTTAIPLFAVQNYQVPLLS
eCry3.1Ab  103 Q.NVED.VSALSS.QKN.AAPFR..HSQGRI.EL.SQAE.HFRNSM.S..ISG.E.LF.T

Cry1Ab     160 VYVQAANLHLSVLRDVSVFGQRWGFDAATINSRYNDLTRLIGNYTDHAVRWYNTGLERVW
eCry3.1Ab  163 T.A....T..FL.K.AQIY.EE..YEKED.AEF.KRQLK.TQE....C.K...V..DKLR

Cry1Ab     220 GPDSRDWIRYNQFRRELTLTVLDIVSLFPNYDSRTYPIRTVSQLTREIYTNPVL--ENFD
eCry3.1Ab  223 .SSYES.VNF.RY..M.....LIA....L.V.L..KEVKTE..DVL.D.IVGVN.LR

Cry1Ab     278 GSFRGSAQGIEGSIRSPHLMDILNSITIYTDAHRGEY-----YWSGHQIMASPVGFSGP
eCry3.1Ab  283 -YGTTFSN..NY..K..F.Y.HR.QFH.RFQP.Y.GNDSFN...NYVSTR.SIG.ND

Cry1Ab     332 EFTFPLYGTMGNAAPQQRIVAQLGQVYRTLSST---LYRRPFNIGINNQQLSVL-DGTE
eCry3.1Ab  342 II.S.F..NK-SSE.V.NLEFN-..EK...AVAN.NLAVWPSAVYS.VTKVEF.QYN.Q.D

Cry1Ab     388 FA----YGTSSNLPSAVYRKSGTVDSLDEIPPQNNNVPPRQGFSHRLSHVSMFRSGFSNS
eCry3.1Ab  400 E.STQT.DSKR.VGAVSW------.I.QL..ETTDE.LEK.Y..Q.NY.MC.LMQG.RG

Cry1Ab     444 SVSIIRAPMFSWIHRSAEFNNIIPSSQITQIPLTKSTNLGSGTSVVKGPGFTGGDILRRT
eCry3.1Ab  454 TI------.VLT.T.K.VD.F.M.D.KK...L..........................
```

Fig. 2A

```
Cry1Ab      504 SPGQISTLRVNITAPLSQRYRVRIRYASTTNLQFHTSIDGRPINQGNFSATMSSGSNLQS
eCry3.1Ab   509 ............................................................

Cry1Ab      564 GSFRTVGFTTPFNFSNGSSVFTLSAHVFNSGNEVYIDRIEFVPAEVTFEAEYDLERAQKA
eCry3.1Ab   569 ............................................................

Cry1Ab      624 VNELFTSSNQIGLKTDVTDYHIDQVSNLVECLSDEFCLDEKKELSEKVKHAKRLSDERNL
eCry3.1Ab   629 .........................-----------------------------------

Cry1Ab      684 LQDPNFRGINRQLDRGWRGSTDITIQGGDDVFKENYVTLLGTFDECYPTYLYQKIDESKL
eCry3.1Ab   654 ------------------------------------------------------------

Cry1Ab      744 KAYTRYQLRGYIEDSQDLEIYLIRYNAKHETVNVPGTGSLWPLSAPSPIGKCAHHSHHFS
eCry3.1Ab   654 ------------------------------------------------------------

Cry1Ab      804 LDIDVGCTDLNEDLGVWVIFKIKTQDGHARLGNLEFLEEKPLVGEALARVKRAEKKWRDK
eCry3.1Ab   654 ------------------------------------------------------------

Cry1Ab      864 REKLEWETNIVYKEAKESVDALFVNSQYDRLQADTNIAMIHAADKRVHSIREAYLPELSV
eCry3.1Ab   654 ------------------------------------------------------------

Cry1Ab      924 IPGVNAAIFEELEGRIFTAFSLYDARNVIKNGDFNNGLSCWNVKGHVDVEEQNNHRSVLV
eCry3.1Ab   654 ------------------------------------------------------------

Cry1Ab      984 VPEWEAEVSQEVRVCPGRGYILRVTAYKEGYGEGCVTIHEIENNTDELKFSNCVEEEVYP
eCry3.1Ab   654 ------------------------------------------------------------
```

Fig. 2B

```
Cry1Ab       1044 NNTVTCNDYTATQEEYEGTYTSRNRGYDGAYESNSSVPADYASAYEEKAYTDGRRDNPCE
eCry3.1Ab     654 ------------------------------------------------------------

Cry1Ab       1104 SNRGYGDYTPLPAGYVTKELEYFPETDKVWIEIGETEGTFIVDSVELLLMEE
eCry3.1Ab     654 ----------------------------------------------------
```

Fig. 2C

```
Cry1Ab        1 MDNNPNINECIPYNCLSNPEVEVLGGERIETGYTPIDISLSLTQFLLSEFVPGAGFVLGL
Cry1A.105     1 ............................................................

Cry1Ab       61 VDIIWGIFGPSQWDAFLVQIEQLINQRIEEFARNQAISRLEGLSNLYQIYAESFREWEAD
Cry1A.105    61 ............................................................

Cry1Ab      121 PTNPALREEMRIQFNDMNSALTTAIPLFAVQNYQVPLLSVYVQAANLHLSVLRDVSVFGQ
Cry1A.105   121 ............................................................

Cry1Ab      181 RWGFDAATINSRYNDLTRLIGNYTDHAVRWYNTGLERVWGPDSRDWIRYNQFRRELTLTV
Cry1A.105   181 ............................................................

Cry1Ab      241 LDIVSLFPNYDSRTYPIRTVSQLTREIYTNPVLENFDGSFRGSAQGIEGSIRSPHLMDIL
Cry1A.105   241 ............................................................

Cry1Ab      301 NSITIYTDAHRGEYYWSGHQIMASPVGFSGPEFTFPLYGTMGNAAPQQRIVAQLGQGVYR
Cry1A.105   301 ............................................................

Cry1Ab      361 TLSSTLYRRPFNIGINNQQLSVLDGTEFAYGTSSNLPSAVYRKSGTVDSLDEIPPQNNNV
Cry1A.105   361 ............................................................

Cry1Ab      421 PPRQGFSHRLSHVSMFRSGFSNSSVSIIRAPMFSWIHRSAEFNNIIPSSQITQIPLTKST
Cry1A.105   421 ..............................................A.DS......V.AH

Cry1Ab      481 NLGSGTSVVKGPGFTGGDILRRTSPGQISTLRVNITAPLSQRYRVRIRYASTTNLQFHTS
Cry1A.105   481 T.Q...T..R...............G.PFAYTI...NGQ.P....A.........RIYVT
```

Fig. 3A

```
Cry1Ab        541 IDGRPINQGNFSATMSSGSNLQSGSFRTVGFTTPFNFSNGSSVFTLSAHVFNSGNEVYID
Cry1A.105     541 VA.ER.FA.Q.NK..DT.DP.TFQ..SYATIN.A.T.PMSQ.S..VG.DT.S........

Cry1Ab        601 RIEFVPAEVTFEAEYDLERAQKAVNELFTSSNQIGLKTDVTDYHIDQVSNLVECLSDEFC
Cry1A.105     601 .F.LI.VTA.L....N.........A....T..L....N..............TY......

Cry1Ab        661 LDEKKELSEKVKHAKRLSDERNLLQDPNFRGINRQLDRGWRGSTDITIQGGDDVFKENYV
Cry1A.105     661 ....R.....................S..KD....PE...G...G...............

Cry1Ab        721 TLLGTFDECYPTYLYQKIDESKLKAYTRYQLRGYIEDSQDLEIYLIRYNAKHETVNVPGT
Cry1A.105     721 ..S......................F..................S...............

Cry1Ab        781 GSLWPLSAPSPIGKC--------------------------AHHSHHFSLDIDVGCTDLN
Cry1A.105     781 ........Q......GEPNRCAPHLEWNPDLDCSCRDGEKC...................

Cry1Ab        815 EDLGVWVIFKIKTQDGHARLGNLEFLEEKPLVGEALARVKRAEKKWRDKREKLEWETNIV
Cry1A.105     841 ............................................................

Cry1Ab        875 YKEAKESVDALFVNSQYDRLQADTNIAMIHAADKRVHSIREAYLPELSVIPGVNAAIFEE
Cry1A.105     901 ..................Q.........................................

Cry1Ab        935 LEGRIFTAFSLYDARNVIKNGDFNNGLSCWNVKGHVDVEEQNNHRSVLVVPEWEAEVSQE
Cry1A.105     961 ...........................................Q................

Cry1Ab        995 VRVCPGRGYILRVTAYKEGYGEGCVTIHEIENNTDELKFSNCVEEEVYPNNTVTCNDYTA
Cry1A.105    1021 ..............................................I............V
```

Fig. 3B

```
Cry1Ab   1055  TQEEYEGTYTSRNRGYDGAYESNSSVPADYASAYEEKAYTDGRRDNPCESNRGYGDYTPL
Cry1A.105 1081 N...G.A.......NE.----P........V.....S.....E....F....R......

Cry1Ab   1115  PAGY

```
Cry1Ab         1   MDNNPNINECIPYNCLSNPEVEVLGGERIETGYTPIDISLSLTQFLLSEFVPGAGFVLGL
H04-Cry1Ab     1   ............................................................

Cry1Ab        61   VDIIWGIFGPSQWDAFLVQIEQLINQRIEEFARNQAISRLEGLSNLYQIYAESFREWEAD
H04-Cry1Ab    61   ............................................................

Cry1Ab       121   PTNPALREEMRIQFNDMNSALTTAIPLFAVQNYQVPLLSVYVQAANLHLSVLRDVSVFGQ
H04-Cry1Ab   121   ............................................................

Cry1Ab       181   RWGFDAATINSRYNDLTRLIGNYTDHAVRWYNTGLERVWGPDSRDWIRYNQFRRELTLTV
H04-Cry1Ab   181   ............................................................

Cry1Ab       241   LDIVSLFPNYDSRTYPIRTVSQLTREIYTNPVLENFDGSFRGSAQGIEGSIRSPHLMDIL
H04-Cry1Ab   241   ............................................................

Cry1Ab       301   NSITIYTDAHRGEYYWSGHQIMASPVGFSGPEFTFPLYGTMGNAAPQQRIVAQLGQGVYR
H04-Cry1Ab   301   ............................................................

Cry1Ab       361   TLSSTLYRRPFNIGINNQQLSVLDGTEFAYGTSSNLPSAVYRKSGTVDSLDEIPPQNNNV
H04-Cry1Ab   361   ............................................................

Cry1Ab       421   PPRQGFSHRLSHVSMFRSGFSNSSVSIIRAPMFSWIHRSAEFNNIIPSSQITQIPLTKST
H04-Cry1Ab   421   ........................................TLT.T.DPER.N....V.GF

Cry1Ab       481   NLGSGTSVVKGPGFTGGDILRRTSPGQISTLRVNITAPLSQRYRVRIRYASTTNLQF---
H04-Cry1Ab   481   RVWG....IT............NTF.DFVS.Q...NS.IT....L.F....SRDARVIVL
```

Fig. 4A

```
Cry1Ab       538 ----HTSIDGRPINQGNFSATMSSGSNLQSGSFRTVGFTTPFNFSNGSSVFTLSAH-VFN
H04-Cry1Ab   541 TGAAS.GVG.QVSVNMPLQK..EI.E..T.RT..YTD.SN..S.RANPDIIGI.EQPL.G

Cry1Ab       593 SGN----EVYIDRIEFVPAEVTFEAEYDLERAQKAVNELFTSSNQIGLKTDVTDYHIDQV
H04-Cry1Ab   601 A.SISSG.L...K..IIL.DA.....S..........A......................

Cry1Ab       649 SNLVECLSDEFCLDEKKELSEKVKHAKRLSDERNLLQDPNFRGINRQLDRGWRGSTDITI
H04-Cry1Ab   661 ....D.......................................................

Cry1Ab       709 QGGDDVFKENYVTLLGTFDECYPTYLYQKIDESKLKAYTRYQLRGYIEDSQDLEIYLIRY
H04-Cry1Ab   721 ..............Q.............P...............................

Cry1Ab       769 NAKHETVNVPGTGSLWPLSAPSPIGKC--------------------------AHHSHHF
H04-Cry1Ab   781 ...........................GEPNRCAPHLEWNPDLDCSCRDGEKC.......

Cry1Ab       803 SLDIDVGCTDLNEDLGVWVIFKIKTQDGHARLGNLEFLEEKPLVGEALARVKRAEKKWRD
H04-Cry1Ab   841 ............................................................

Cry1Ab       863 KREKLEWETNIVYKEAKESVDALFVNSQYDRLQADTNIAMIHAADKRVHSIREAYLPELS
H04-Cry1Ab   901 ............................................................

Cry1Ab       923 VIPGVNAAIFEELEGRIFTAFSLYDARNVIKNGDFNNGLSCWNVKGHVDVEEQNNHRSVL
H04-Cry1Ab   961 ............................................................

Cry1Ab       983 VVPEWEAEVSQEVRVCPGRGYILRVTAYKEGYGEGCVTIHEIENNTDELKFSNCVEEEVY
H04-Cry1Ab  1021 ............................................................
```

Fig. 4B

```
Cry1Ab         1043 PNNTVTCNDYTATQEEYEGTYTSRNRGYDGAYESNSSVPADYASAYEEKAYTDGRRDNPC
H04-Cry1Ab     1081 ............................................................

Cry1Ab         1103 ESNRGYGDYTPLPAGYVTKELEYFPETDKVWIEIGETEGTFIVDSVELLLMEE
H04-Cry1Ab     1141 ................................................II...
```

Fig. 4C

COMPOSITIONS AND METHODS FOR DETECTION OF WILD TYPE CRY PROTEIN AND A HYBRID CRY PROTEIN

CROSS-REFERENCE TO RELATED APPLICATIONS

This application is a divisional of co-pending U.S. application Ser. No. 15/755,721, filed Feb. 27, 2018, which is a 35 U.S.C. § 371 National Stage application of PCT Application No. PCT/US16/48580, filed Aug. 25, 2016, and published as WO2017/044310 on Mar. 16, 2017, which claims the benefit of U.S. Provisional Application No. 62/215,982, filed Sep. 9, 2015, all of which are incorporated by reference herein in their entirety.

REFERENCE TO SEQUENCE LISTING SUBMITTED ELECTRONICALLY

The official copy of the sequence listing is submitted electronically via EFS-Web as an ASCII formatted sequence listing with a file named "80859-US-REG-ORG-P-1_SeqList_ST25.txt", originally created on Sep. 8, 2015, and having a size of 48 kilobytes and is filed concurrently with the specification. The sequence listing contained in this ASCII formatted document is part of the specification and is herein incorporated by reference in its entirety.

FIELD OF THE INVENTION

The invention relates generally to immunoassays, and more particularly to monoclonal antibodies and immunoassays for the differential detection and quantitation of wild-type crystal proteins from *Bacillus thuringiensis* and hybrid crystal proteins in complex biological samples.

BACKGROUND

*Bacillus thuringiensis* is a ubiquitous gram-positive, spore-forming bacterium that forms a crystalline protein inclusion during the stationary phase of its growth cycle. The crystal proteins (Cry proteins) are toxic to a number of plant pests, including many insects in the orders Lepidoptera and Coleoptera. Prior to 1990, the major Cry protein classes were defined by their spectrum of activity with the Cry1 proteins active against Lepidoptera (moths and butterflies), Cry2 proteins active against both Lepidoptera and Diptera (flies and mosquitoes), Cry3 proteins active against Coleoptera (beetles) and Cry4 proteins active against Diptera (Hofte and Whitely, 1989, Microbiol. Rev. 53:242 255). Subsequent to the Hofte and Whitely nomenclature scheme, a different nomenclature was developed which systematically classifies the Cry proteins based on amino acid sequence homology rather than insect target specificities (Crickmore et al. 1998, Microbiol. Mol. Biol. Rev. 62:807 813).

Most Cry proteins active against lepidopteran or coleopteran insects are formed in the crystalline matrix as 130-140 kDa or 60-70 kDa protoxins, respectively. In lepidopteran insects, the alkaline pH of the gut solubilizes the crystal and then gut proteases process the 130-140 kDa protoxin to toxic proteins of approximately 60-70 kDa. In coleopteran insects, the 60-70 kDa protoxins are processed to 55-67 kDa toxins. Examples of lepidopteran-active Cry proteins include Cry1A, Cry1B, Cry1C, Cry1D, Cry1E, Cry1F and Cry9. Examples of coleopteran-active Cry proteins include, Cry3A, Cry3B, Cry3C, Cry8, the binary Cry23-Cry37 and the binary Cry34-Cry35. Processing of the Cry protein protoxin to a toxin has been reported to proceed by removal of both N- and C-terminal amino acids with the exact location of processing being dependent on the specific Cry protein and the specific insect gut fluids involved (Ogiwara et al., 1992. J. Invert. Pathol. 60:121-126). The proteolytic activation of a Cry protoxin can play a significant role in determining its specificity.

All or parts of certain wild-type Cry proteins have been used to engineer hybrid Cry proteins in attempts to create insecticidal proteins with improved specific activity or broader spectrum of insecticidal activity. Targeted engineering was made more possible by solving the three dimensional structure of Cry3A by Li el al. (1991, Nature 353: 815-821). Based on this work, it has been determined that Cry proteins in general have three structural domains: the N-terminal domain I, from residues 1-290, consists of 7 alpha helices, domain II, from residues 291-500, contains three beta-sheets and the C-terminal domain III, from residues 501-644, is a beta-sandwich. Based on this structure, a hypothesis has been formulated regarding the structure/function relationship of the Cry proteins. It is generally thought that domain I is primarily responsible for pore formation in the insect gut membrane (Gazit and Shai, 1993, Appl. Environ. Microbiol. 57:2816 2820), domain II is primarily responsible for interaction with the gut receptor (Ge el al., 1991, J. Biol. Chem. 32:3429 3436) and that domain III is most likely involved with protein stability (Li et al. 1991, supra) as well as having a regulatory impact on ion channel activity (Chen et al., 1993, PNAS 90:9041 9045).

Many successful attempts to create hybrid Cry proteins have been disclosed in the literature. For example, the silk moth (*Bombyx mori*) specificity domain from a Cry1Aa protein was moved to a Cry1Ac protein, thus imparting a new insecticidal activity to the resulting Cry1Aa-Cry1Ac chimeric protein (Ge et al. 1989, PNAS 86: 4037 4041). Thompson et al. 1996 and 1997 (U.S. Pat. Nos. 5,527,883 and 5,593,881) replaced the protoxin tail region of a wild-type Cry1F protein and Cry1C protein with the protoxin tail region of a Cry1Ab protein to make a Cry1F-Cry1Ab hybrid Cry protein and a Cry1C-Cry1Ab hybrid Cry protein, both having improved expression in certain expression host cells. Bosch et al. 1998 (U.S. Pat. No. 5,736,131), created new lepidopteran-active proteins by substituting domain III of a Cry1Ea protein and a Cry1Ab protein with domain III of Cry1Ca protein thus producing a Cry1E-Cry1C hybrid Cry protein called G27 and a Cry1Ab-Cry1C hybrid Cry protein called H04, both of which have a broader spectrum of lepidopteran activity than the wild-type Cry protein parent molecules. Malvar et al. 2001 (U.S. Pat. No. 6,242,241) combined domain I of a Cry1Ac protein with domains II and III and the protoxin tail of a Cry1F protein to create a Cry1Ac-Cry1F hybrid Cry protein with broader insecticidal activity than the parental wild-type Cry proteins. Bogdanova et al. 2011 (U.S. Pat. No. 8,034,997) combined domains I and II of a Cry1Ab protein with domain III of a Cry1Fa protein and added a Cry1Ac protein protoxin tail to create a new lepidopteran-active hybrid Cry protein called Cry1A.105. And, Hart et al. 2012 (U.S. Pat. No. 8,309,516) combined domains I and II of a modified Cry3A protein with domain III of a Cry1Ab protein and added a portion of a Cry1Ab protein protoxin tail to create a coleopteran-active hybrid Cry protein called FR8a (also called eCry3.1Ab). Most of the reported hybrid Cry proteins to date have used all or parts of the same classes of wild-type Cry proteins, such as Cry1Aa, Cry1Ab, Cry1Ac, Cry1C, Cry1F and Cry3A.

Several wild-type Cry proteins, for example Cry1Ab, Cry1Ac, Cry1C, Cry1F, Cry2A, Cry2Ba, Cry3A, Cry3B, Cry9C, and Cry34-Cry35 have been expressed in transgenic crop plants, including corn, cotton, rice and soybean, some of which have been exploited commercially to control certain lepidopteran and coleopteran insect pests since as early as 1996. More recently, transgenic crop products containing hybrid Cry proteins, for example Cry1A.105 (Cry1Ab-Cry1F-Cry1Ac) and eCry3.1Ab (mCry3A-Cry3A-Cry1Ab), have been introduced commercially.

Immunoassay is the current preferred method in the agricultural industry for detection and quantification of Cry proteins introduced through genetic modification of plants. The crucial component of an immunoassay is an antibody with specificity for the target molecule (antigen). Immunoassays can be highly specific and samples often need only a simple preparation before being analyzed. Moreover, immunoassays can be used qualitatively or quantitatively over a wide range of concentrations. Typically, immunoassays require separate tests for each Cry protein of interest.

The antibodies can be polyclonal, raised in animals, or monoclonal, produced by cell cultures. Commercially available polyclonal antiserum is often produced in rabbits, goats or sheep. Monoclonal antibodies offer some advantages over polyclonal antibodies because they express uniform affinity and specificity against a single epitope or antigenic determinant and can be produced in vast quantities. Both polyclonal and monoclonal antibodies may require further purification steps to enhance the sensitivity and reduce backgrounds in assays.

Making a valid identification of a product containing a Cry protein or quantitating a Cry protein in a commercial product depends on the accuracy of the immunoassay. Development of a successful immunoassay depends on certain characteristics of the antigen used for development of the antibody, i.e. size, hydrophobicity and the tertiary structure of the antigen. The specificity of the antibodies must be checked carefully to elucidate any cross-reactivity with similar substances, which might cause false positive results. A current problem in the industry is that many of the antibodies in commercially available tests kits do not differentiate between various products or wild-type Cry proteins, making differential product identification and quantitation difficult or impossible.

With many current commercial transgenic crop products using one or more of the same wild-type Cry proteins, for example Cry1Ab, Cry1F and Cry3, and with the introduction of crops expressing hybrid Cry proteins made of whole or parts of the same wild-type Cry proteins that are already in transgenic crop products, there is a continuing need to develop new and improved immunoassays to be able to distinguish a wild-type Cry protein from a hybrid Cry protein containing all or portions of that same wild-type Cry protein when they are together in complex biological samples, such as samples from transgenic plants.

SUMMARY

The present invention addresses the need for new and improved immunoassays by providing compositions useful in specific detection and differentiation of certain wild-type Cry proteins and engineered hybrid Cry proteins comprising all or part of the wild-type Cry protein amino acid sequence in complex biological samples, including transgenic plant samples. The invention also relates to methods, assays and kits to specifically detect and differentiate wild-type Cry proteins from engineered hybrid Cry proteins comprising all or part of the wild-type Cry protein amino acid sequence in biological samples comprising the wild-type Cry protein and the hybrid Cry protein.

According to one aspect, the invention provides a composition comprising a first antibody and a second antibody that function together to specifically detect or quantitate a Cry1Ab protein in an immunoassay of a biological sample comprising the Cry1Ab protein and a hybrid Cry protein having at least a contiguous 27% of the Cry1Ab protein's amino acid sequence, wherein the first antibody and the second antibody individually are capable of binding to both the wild-type Cry1Ab protein and the hybrid Cry protein.

According to another aspect, the invention also provides a pair of purified antibodies comprising a first antibody and a second antibody that function together in an immunoassay to specifically detect or quantitate a Cry1Ab protein in a biological sample comprising the Cry1Ab protein and a hybrid Cry protein having at least a contiguous 27% of the Cry1Ab protein's amino acid sequence, wherein the first antibody and the second antibody individually are capable of binding to both the Cry1Ab protein and the hybrid Cry protein.

According to yet another aspect of this invention, a diagnostic kit is provided for detecting a Cry1Ab protein in a biological sample which comprises the Cry1Ab protein and a hybrid Cry protein having at least a contiguous 27% of the Cry1Ab protein's amino acid sequence, wherein the kit comprises a first antibody and a second antibody that function together to specifically detect or quantitate the Cry1Ab protein and that individually are capable of binding both the Cry1Ab protein and the hybrid Cry protein.

In certain embodiments of the above described aspects of the invention, the immunoassay is a enzyme-linked immunosorbent assay (ELISA), preferably a sandwich ELISA. In other embodiments of these aspects of the invention, the first antibody is the coating antibody and the second antibody is the detecting antibody. In still other embodiments, the first and the second antibodies are monoclonal. In yet other embodiments, the first or coating antibody is the monoclonal antibody 87AB1.1, which is available from Romer Labs, Inc (Union, Mo.). In still other embodiments, the second or detecting antibody is the monoclonal antibody H04MAb70 produced by the hybridoma cell line H04MAb70 deposited as ATCC Accession No. PTA-122984. In yet other embodiments, the coating antibody is 87AB1.1 and the detecting antibody is H04MAb70.

In other embodiments of the above described aspects of the invention, the Cry1Ab protein comprises an amino acid sequence represented by SEQ ID NO:1, SEQ ID NO:2 or SEQ ID N:6. In other embodiments, the hybrid Cry protein is eCry3.1Ab, the amino acid sequence of which is set forth in SEQ ID NO:3, H04, the amino acid sequence of which is set forth in SEQ ID NO:4 or Cry1A.105, the amino acid sequence of which is set forth in SEQ ID NO:5.

In other embodiments of the above described aspects of the invention, the biological sample is a transgenic plant sample. In other embodiments, the transgenic plant is a transgenic corn plant comprising a transgenic event selected from the group consisting of event Bt11, which comprises the Cry1Ab protein of SEQ ID NO:1, event 5307, which comprises the eCry3.1Ab hybrid Cry protein of SEQ ID NO:3, event MON89034, which comprises the Cry1A.105 hybrid Cry protein of SEQ ID NO:5 and event MON810, which comprises the Cry1Ab protein of SEQ ID NO:6.

According to another aspect of the invention, there is provided a hybridoma cell line, designated H04MAb70, deposited as ATCC Accession No. PTA-122984, and a hybridoma cell line designated MAb58, deposited as ATCC Accession No. PTA-122985. In certain embodiments of this aspect of the invention, there is provided a monoclonal antibody designated H04MAb70 produced by the H04MAb hybridoma cell line that binds to both a wild-type Cry1Ab protein and a hybrid Cry protein. In certain other embodiments of this aspect of the invention, there is provided a monoclonal antibody designated MAb58 produced by the hybridoma cell line MAb58 that binds to a hybrid Cry protein.

According to another aspect of the invention there is provided immunoassay methods to specifically detect or quantitate a Cry1Ab protein in a biological sample comprising the Cry1Ab protein and a hybrid Cry protein having at least a contiguous 27% of the Cry1Ab protein's amino acid sequence. Such methods comprise (a) obtaining a biological sample comprising the Cry1Ab protein and the hybrid Cry protein; and (b) performing an immunoassay on the biological sample, wherein the immunoassay comprises use of a first antibody and a second antibody that individually are capable of binding to the Cry1Ab protein and the hybrid Cry protein but that function together in the immunoassay to specifically detect or quantitate the Cry1Ab protein and not the hybrid Cry protein, resulting in the specific detection or quantitation of the Cry1Ab protein.

In some embodiments of this aspect, the immunoassay is an enzyme-linked immunosorbent assay (ELISA). In other embodiments, the first antibody is a coating antibody and the second antibody is a detecting antibody. In further embodiments, the coating antibody and the detecting antibody are monoclonal. In still other embodiments, the coating antibody is the monoclonal antibody 87AB1.1 available from Romer Labs, Inc. (Union, Mo.). In yet other embodiments, the detecting antibody is the monoclonal antibody H04MAb70 produced by the hybridoma cell line deposited as ATCC Accession No. PTA-122984. In other embodiments, the coating antibody is 87AB1.1 and the detecting antibody is H04MAb70.

In some embodiments of this aspect of the invention, the Cry1Ab protein comprises an amino acid sequence selected from the group consisting of SEQ ID NO:1, SEQ ID NO:2 and SEQ ID NO:6. In other embodiments, the hybrid Cry protein is selected from the group consisting of eCry3.1Ab (SEQ ID NO:3), Cry1A.105 (SEQ ID NO:4) and H04 (SEQ ID NO:5). In still other embodiments, the Cry1Ab protein comprises the amino acid sequence of SEQ ID NO:1 or SEQ ID NO:2 or SEQ ID NO:6 and the hybrid Cry protein is eCry3.1Ab (SEQ ID NO:3) or Cry1A.105 (SEQ ID NO:4) or H04 (SEQ ID NO:5).

In some embodiments of this aspect of the invention, the biological sample tested in the immunoassay is a transgenic plant sample. In other embodiments, the transgenic plant sample is from a transgenic corn plant. In other embodiments, the transgenic corn plant comprises a transgenic corn event selected from the group consisting of event Bt11, event 5307, event MON89034 and event MON810. In still other embodiments, the transgenic corn plant comprises event Bt11, event 5307 and event MON89034. In yet further embodiments, the biological sample comprises a Cry1Ab protein from event Bt11 and an eCry3.1Ab hybrid Cry protein from event 5307 and optionally a Cry1A.105 hybrid Cry protein from event MON89034. In still further embodiments, the biological sample comprises a Cry1Ab protein from event MON810 and a Cry1A.105 hybrid Cry protein from event MON89034.

In another aspect of the invention there is provided immunoassay methods for detecting or quantitating both a Cry1Ab protein and a hybrid Cry protein having at least a contiguous 27% of a Cry1Ab protein's amino acid sequence in a biological sample comprising the hybrid Cry protein and the Cry1Ab protein. Such immunoassay methods comprise: (a) obtaining a biological sample comprising the hybrid Cry protein and the Cry1Ab protein; (b) contacting the biological sample with a first antibody under conditions effective to allow the formation of a Cry1Ab-first antibody complex but not a hybrid Cry protein-first antibody complex, resulting in a biological sample depleted of the Cry1Ab protein; (c) removing the Cry1Ab-depleted biological sample from contact with the first antibody; (d) contacting the Cry1Ab-depleted biological sample with a second antibody under conditions effective to allow the formation of a hybrid Cry protein-second antibody complex; and (e) detecting or quantitating the hybrid Cry protein in the hybrid Cry protein-second antibody complex.

In some embodiments of this aspect, the immunoassay is an enzyme-linked immunosorbent assay, wherein the solid surface is a well in a microtiter dish. In other embodiments, the hybrid Cry protein is eCry3.1Ab (SEQ ID NO:3) or Cry1A.105 (SEQ ID NO:4). In other embodiments, the first antibody is 87AB1.1 which is available from Romer Labs, Inc. (Union, Mo.). In other embodiments, the second antibody is the monoclonal antibody MAb58 produced by the hybridoma cell line deposited as ATCC Accession No. PTA-122985. In yet other embodiments of this aspect, the detecting of step (d) is carried out using a composition comprising a monoclonal antibody capable of binding to the Cry1Ab protein and the hybrid Cry protein. In still further embodiments, the monoclonal antibody is H04MAb70. In yet other embodiments of this aspect, the detecting step (e) is carried out using a composition comprising a monoclonal antibody or a polyclonal antibody capable of binding to the hybrid Cry protein and the Cry1Ab protein. In further embodiments, the monoclonal antibody is H04MAb70 or the polyclonal antibody is PAb713 available from Romer Labs, Inc. (Union, Mo.).

According to yet another aspect of the invention there is provided immunoassay methods to detect or quantitate a hybrid Cry protein having at least a contiguous 27% of a Cry1Ab protein's amino acid sequence in a biological sample comprising the hybrid Cry protein and the Cry1Ab protein. Such methods comprise: (a) obtaining a biological sample comprising the hybrid Cry protein and the Cry1Ab protein; (b) contacting the biological sample with a 87AB1.1 antibody under conditions effective to allow the formation of a Cry1Ab-87AB1.1 complex but not a hybrid Cry protein-87AB1.1 complex, resulting in a biological sample depleted of the Cry1Ab protein; (c) removing the Cry1Ab-depleted biological sample from contact with the 87AB1.1 antibody; (d) contacting the Cry1Ab-depleted biological sample with a second antibody under conditions effective to allow the formation of a hybrid Cry protein-second antibody complex; and (e) detecting or quantitating the hybrid Cry protein in the hybrid Cry protein-second antibody complex.

In some embodiments of this aspect, the hybrid Cry protein is eCry3.1Ab (SEQ ID NO:3) or Cry1A.105 (SEQ ID NO:4).

In other embodiments, the biological sample is from a transgenic plant. In some other embodiments, the transgenic plant is a transgenic corn plant. In still other embodiments, the transgenic corn plant comprises a transgenic corn event selected from the group consisting of event Bt11, event 5307, event MON89034 and event MON810. In yet other embodiments, the transgenic corn plant comprises the transgenic corn event Bt11, event 5307 and event MON89034. In other embodiments, the transgenic corn plant comprises the transgenic event MON810 and the transgenic event MON89034. In other embodiments, the biological sample comprises a Cry1Ab protein from event Bt11 and an eCry3.1Ab hybrid Cry protein from event 5307 and optionally, a Cry1A.105 hybrid Cry protein from event MON89034. In still further embodiments, the biological sample comprises a Cry1Ab protein from event MON810 and a Cry1A.105 hybrid Cry protein from event MON89034.

Various objects, features, aspects, and advantages of the present invention will become more apparent from the following detailed description of preferred embodiments of the invention, along with the accompanying drawings and sequence listing.

BRIEF DESCRIPTION OF THE FIGURES

FIG. 2 is an amino acid sequence alignment between wild-type Cry1Ab and an eCry3.1Ab hybrid Cry protein. The amino acids in eCry3.1Ab, amino acids 480-653, that are a contiguous 27% of the Cry1Ab protein are underlined.

FIG. 3 is an amino acid alignment between a wild-type Cry1Ab and a Cry1A.105 hybrid Cry protein. The amino acids in Cry1A.105, amino acids 1-467, that are a contiguous 40% of the Cry1Ab protein are underlined.

FIG. 4 is an amino acid alignment between a wild-type Cry1Ab and a H04 hybrid Cry protein. The amino acids in H04, amino acids 1-460 and 832-1188, that are a contiguous 30% and 39%, respectively, of the Cry1Ab protein are underlined. The H04 protein comprises a total of 69% of wild-type Cry1Ab amino acids.

BRIEF DESCRIPTION OF THE SEQUENCES IN THE SEQUENCE LISTING

Figure 1:
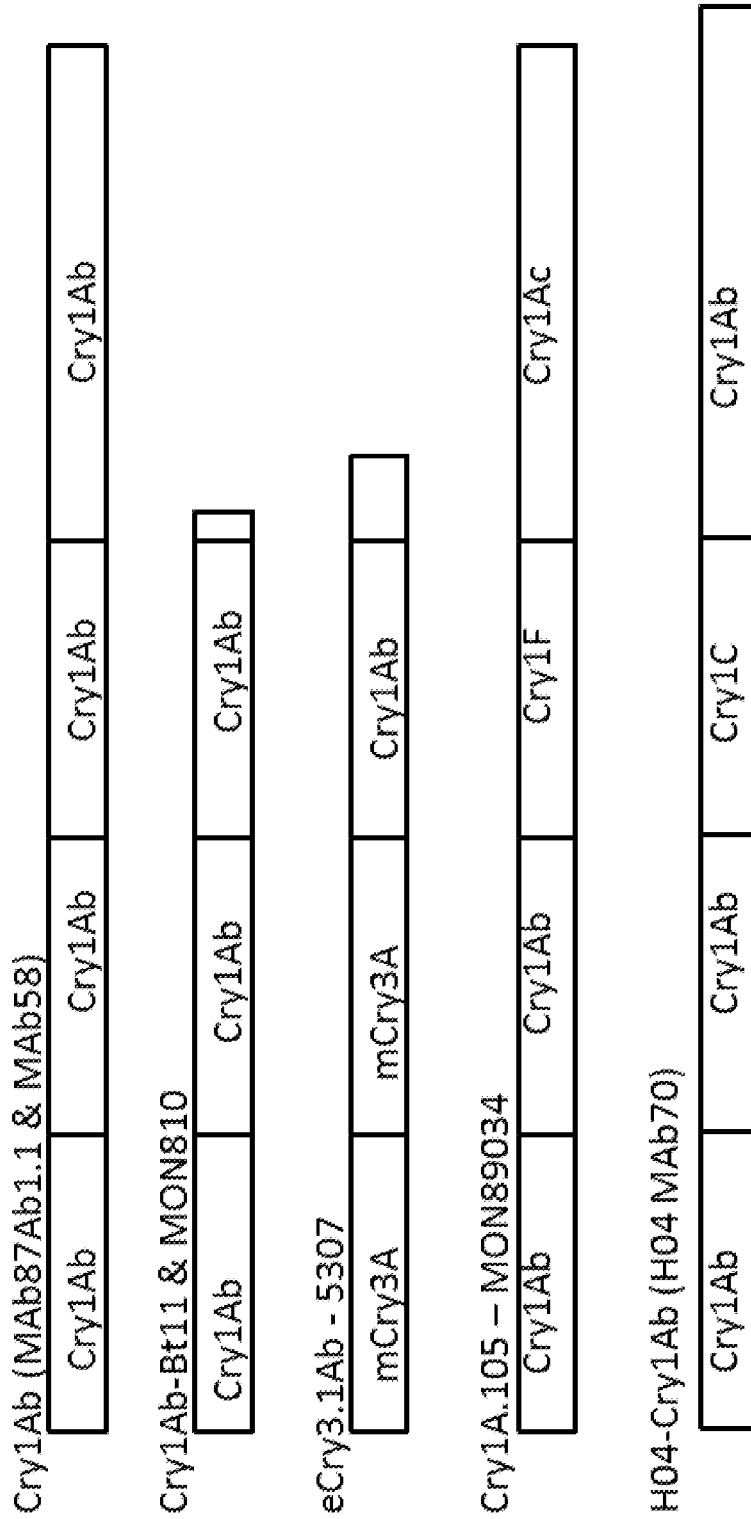
FIG. 1 is a graphic of the structure of wild-type Cry1Ab proteins and hybrid Cry proteins having at least a contiguous 27% of the Cry1Ab protein's amino acid sequence showing the relationship of the Cry1Ab portions of the hybrid Cry proteins and the wild-type Cry1Ab proteins. Proteins used to make antibodies of the invention are indicated as well as proteins in commercial transgenic corn events.

SEQ ID NO:1 is an amino acid sequence of a wild-type Cry1Ab protein expressed in the transgenic corn event B tn.

SEQ ID NO:2 is an amino acid sequence of a wild-type Cry1Ab protein used to make the MAb58 monoclonal antibody.

SEQ ID NO:3 is an amino acid sequence of a eCry3.1Ab hybrid Cry protein expressed in the transgenic corn event 5307.

SEQ ID NO:4 is an amino acid sequence of a Cry1A.105 hybrid Cry protein expressed in the transgenic corn event MON89034.

SEQ ID NO:5 is an amino acid sequence of a H04 hybrid Cry used to make the H04MAb70 monoclonal antibody.

SEQ ID NO:6 is an amino acid sequence of a wild-type Cry1Ab protein expressed in the transgenic corn event MON810.

DEPOSITS

Hybridoma cell line H04MAb70 and Hybridoma cell line MAb58 were deposited with the American Type Culture Collection, 10801 University Blvd., Manassas, Va., on Mar. 30, 2016 and have the following accession numbers: HO4Mab70: PTA-122984 and Mab58: PTA-122985. Both deposits were made under the terms of the Budapest Treaty on the International Recognition of the Deposit of Microorganisms for the Purposes of Patent Procedure. All restrictions on the availability of the deposited material will be irrevocably removed upon granting of the patent.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. It is also to be understood that the terminology used herein is for the purpose of describing particular embodiments only, and is not intended to limit the scope of the present invention.

Definitions

As used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed below. In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "antigen" as used herein means a protein used to trigger an immune response in an organism for the production of an antibody. Antigens according to the present invention include wild-type Cry1Ab proteins and hybrid Cry proteins.

The terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

The term "contacting" refers to a combining action that brings an antibody of the invention into contact with the biological sample and more particularly to a combining action which brings the antibody into contact with the Cry1Ab protein or hybrid Cry protein in a manner that a binding interaction will occur between the antibody and the Cry1Ab protein present in the biological sample.

The term "cross-reactivity" refers to the ability of an antibody to bind a target protein other than that against which it was raised.

The term "depleted" as used herein means that all or a significant portion of a target protein has been removed from a complex biological sample by contacting the biological sample with an antibody that binds to the target protein. A biological sample that has been "depleted" of the target protein has 100% of the target protein removed, or at least 95% of the target protein removed, or at least 90%, or at least 85%, or at least 80% of the target protein removed. Thus, for example, a biological sample of the invention comprising Cry1Ab, eCry3.1Ab and Cry1A.105 that has been depleted of Cry1Ab, has at least 80% to 100% of the Cry1Ab protein removed.

"Detecting antibodies" and "labeled antibodies/labeling antibody" refer to antibodies that are capable of being discovered. The detecting antibody may be directly or indirectly (e.g. through another antibody) conjugated to a detectable signal or to a signal-generating moiety. The signal can be radioactive (e.g. radioactive iodine, tritium, carbon, sulfur or the like), colorimetric, fluorescent signal and the like. Signal-generating moieties that act on signal-generating substrates include, but are not limited to, horseradish peroxidase (HRP) [suitable substrates include 3,3',5,5'-tetramethylbenzidine (TMB); OPD; 2,2'-azinobis(3-ethylbenzothiazoline)-6-sulfonic acid diammonium salt]; alkaline phosphatase [suitable substrates include p-nitrophenyl phosphate disodium salt]; and .beta.-galactosidase [suitable substrates include O-nitrophenyl-beta-D-galactopyranoside]. The signal may be amplified by using an Avidin-Biotin conjugation system.

As used herein the term transgenic "event" refers to a recombinant plant produced by transformation and regeneration of a single plant cell with heterologous DNA, for example, an expression cassette that includes a gene of interest. The term "event" refers to the original transformant and/or progeny of the transformant that include the heterologous DNA. The term "event" also refers to progeny produced by a sexual outcross between the transformant and another corn line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Non-limiting examples of such transgenic events include "event Bt11" (also Bt11 event or just Bt11), "event 5307" (also 5307 event or just 5307), "event MON810" (also MON810 event or just MON810) and "event MON89034" (also MON89034 event or just MON89034. Thus for example, the term "event Bt11", "Bt11 event" or "Bt11" as used herein means the original Bt11 transformant and/or progeny of the Bt11 transformant, including any plant derived therefrom.

As used herein the term "hybrid Cry protein" is an engineered insecticidal protein that does not exist in nature and at least a portion of which comprises at least a contiguous 27% of a Cry1Ab protein's amino acid sequence. The 27% limitation is calculated by dividing the number of contiguous Cry1Ab amino acids in the hybrid Cry protein divided by the total number of amino acids in the hybrid Cry protein. For example, the hybrid Cry protein, eCry3.1Ab (SEQ ID NO:3) has 174 Cry1Ab amino acids (positions 480-653) and a total of 653 amino acids. Therefore, eCry3A.1Ab has at least a contiguous 27% of a Cry1Ab protein's amino acid sequence. Other examples of a hybrid Cry protein according to the present invention is represented by SEQ ID NO:4 and SEQ ID NO:5.

The term "isolated" nucleic acid molecule, polynucleotide or toxin is a nucleic acid molecule, polynucleotide or toxic protein that no longer exists in its natural environment. An isolated nucleic acid molecule, polynucleotide or toxin of the invention may exist in a purified form or may exist in a recombinant host such as in a transgenic bacterial cell or a transgenic plant.

The term "monoclonal antibody" refers to an antibody that is derived from a single clone, including any eukaryotic, prokaryotic, or phage clone, and not the method by which it is produced. The term "monoclonal antibody" as used herein is not limited to antibodies produced through hybridoma technology. Monoclonal antibodies can be prepared using a wide variety of techniques known in the art including the use of hybridoma, recombinant, and phage display technologies, or a combination thereof. For example, it is preferred that monoclonal antibodies of the present disclosure be produced using hybridoma techniques including those known in the art and taught, for example, in Harlow et al., Antibodies: A Laboratory Manual (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). Methods for producing and screening for specific antibodies using hybridoma technology are routine and well known in the art. Briefly, mice can be immunized with the antigen of interest. In a preferred embodiment, the antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue A "wild-type Cry1Ab protein" means a naturally occurring Cry1Ab protein or a Cry1Ab protein with minimal amino acid additions or substitutions to a naturally occurring Cry1Ab amino acid and having the same or similar insecticidal activity or spectrum as the naturally occurring Cry1Ab protein. A "wild-type Cry1Ab protein" can be either a full-length protein or the truncated toxin portion thereof. For example, without limitation, wild-type Cry1Ab proteins according to the present invention include the Cry1Ab protein of SEQ ID NO:1, SEQ ID NO:2 and SEQ ID NO:6.

The present invention provides immunoassay methods and compositions and kits useful in carrying out the immunoassay methods that allow for the specific detection of a Cry1Ab protein in complex biological samples comprising the Cry1Ab protein and at least one hybrid Cry protein having a contiguous at least 27% of the Cry1Ab protein's amino acid sequence. The current state of the art is such that commercially available immunoassays are not useful in differentially detecting a Cry1Ab protein from a hybrid Cry protein engineered using a significant amount of the Cry1Ab protein's amino acid sequence when the two proteins are in the same biological sample because there is high cross-reactivity between the two types of proteins. For example, an antibody raised against a wild-type Cry1Ab for use in a Cry1Ab-detecting immunoassay cross reacts with a hybrid Cry protein having a significant number, e.g. at least 27%, of its amino acids derived from the wild-type Cry1Ab protein when the two proteins are in the same biological sample. Therefore, for example, the quantitation of the wild-type Cry1Ab in such a complex biological sample may be confounded by the presence of one or more hybrid Cry proteins. Furthermore, using detection of expressed proteins for identity preservation of commercial transgenic plant products comprising a wild-type Cry1Ab and one or more hybrid Cry proteins of the present invention is difficult because of cross-reactivity of antibodies to both the Cry1Ab proteins and the hybrid Cry proteins in the transgenic plant products. The methods and compositions disclosed herein provide a solution to these problems and rely on pairs of antibodies, e.g. a first antibody and a second antibody, that alone are capable of binding both a wild-type Cry1Ab protein and a hybrid Cry protein having at least a contiguous 27% of the wild-type Cry1Ab protein's amino acid sequence, but surprisingly function together in an immunoassay of the invention to specifically detect or quantitate the wild-type Cry1Ab protein.

Immunoassays can be carried out in many different formats, examples of which include an enzyme-linked immunosorbent assay (ELISA) and a dipstick format, which is also called a lateral flow stick. In ELISA, the protein antigen-antibody reaction takes place on a solid phase, typically in wells on microtiter plates. Antigen and this first antibody, also called the coating antibody, react and produce a stable complex, which can be visualized by addition of a second antibody, also called the detecting antibody, linked to an enzyme. Addition of a substrate for that enzyme results in a color formation, which can be measured photometrically or recognized by eye.

Dipstick formats (lateral flow sticks) typically use paper strips or plastic paddles as support for the capture antibody and this is then the reaction site. The strip/paddle is dipped in vials containing the different biological samples. Each dip is followed by a rinsing step. The final reaction includes a color change in the vial, where the strip/paddle is placed. Recent development of dipstick format has led to lateral flow techniques where reactants are transported through the channels of a membrane by capillary forces. One single step is enough for performing the assay, and controls for reagent performance are included. Antibodies specific to the foreign protein are coupled to a color reagent and incorporated into the lateral flow strip. When the lateral flow strip is placed in a small amount of a biological sample, for example an extract from plant tissue, that contains foreign protein, binding occurs between the coupled antibody and the protein. A sandwich is formed with some, but not all the antibody that is coupled to the color reagent. The membrane contains two capture zones, one captures the bound foreign protein and the other captures color reagent. These capture zones display a reddish color when the sandwich and/or non-reacted colored reagents are captured in the specific zones on the membrane. The presence of a single line (control line) on the membrane indicates a negative sample and the presence of two lines indicates a positive sample.

In certain embodiments, an antibody as disclosed herein has a detectable label. Detectable labels suitable for use in the detection antibodies of the present invention include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., Dynabeads™), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., 3H, 125I, 35S, 14C, or 32P), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to each antibody prior to, or during, or after contact with the biological sample. So-called "direct labels" are detectable labels that are directly attached to or incorporated into the detection antibody prior to use in the assay. Direct labels can be attached to or incorporated into the antibody by any of a number of means well known to those of skill in the art. In contrast, so-called "indirect labels" typically bind to each antibody at some point during the assay. Often, the indirect label binds to a moiety that is attached to or incorporated into the detection agent prior to use. Thus, for example, each antibody can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to each antibody, as well as to the autoantibodies, labeling all and providing a composite signal attributable to analyte and autoantibody present in the sample.

Some labels useful in the present disclosure may require the use of an additional reagent(s) to produce a detectable signal. In an ELISA, for example, an enzyme label (e.g., beta-galactosidase) will require the addition of a substrate (e.g., X-gal) to produce a detectable signal. In immunoassays using an acridinium compound as the direct label, a basic solution and a source of hydrogen peroxide are added.

According to one embodiment, the invention encompasses a composition comprising a first antibody and a second antibody that function together to specifically detect or quantitate a Cry1Ab protein in an immunoassay of a biological sample comprising the Cry1Ab protein and a hybrid Cry protein having at least a contiguous 27% of the Cry1Ab protein's amino acid sequence, wherein the first antibody and the second antibody individually are capable of binding to both the wild-type Cry1Ab protein and the hybrid Cry protein.

In other embodiments of the invention, the immunoassay is an enzyme-linked immunosorbent assay (ELISA), preferably a sandwich ELISA. In still other embodiments, the first antibody is the coating antibody and the second antibody is the detecting antibody. In still other embodiments, the first and the second antibodies are monoclonal. In yet other embodiments, the first or coating antibody is the monoclonal antibody 87AB1.1 which is available from Romer Labs, Inc (Union, Mo.). In other embodiments, the second or detecting antibody is the monoclonal antibody H04MAb70 produced by the hybridoma cell line H04MAb70 deposited as ATCC Accession No. PTA-122984. In still other embodiments, the coating antibody is 87AB1.1 and the detecting antibody is H04MAb70.

In some embodiments of the invention, the Cry1Ab protein that is specifically detected in an immunoassay of the invention comprises an amino acid sequence represented by SEQ ID NO:1, SEQ ID NO:2 or SEQ ID N:6. In other embodiments, the hybrid Cry protein is eCry3.1Ab, comprising an amino acid sequence set forth in SEQ ID NO:3, Cry1A.105, comprising an amino acid sequence set forth in SEQ ID NO:4, or Cry1A.105, comprising an amino acid sequence set forth in SEQ ID NO:5.

In other embodiments of the invention, the biological sample is a transgenic plant sample. In still other embodiments, the transgenic plant is a transgenic corn plant comprising a transgenic event selected from the group consisting of event Bt11, which expresses the Cry1Ab protein of SEQ ID NO:1, event 5307, which expresses the eCry3.1Ab hybrid Cry protein of SEQ ID NO:3, event MON89034, which expresses the Cry1A.105 hybrid Cry protein of SEQ ID NO:5 and event MON810, which expresses the Cry1Ab protein of SEQ ID NO:6. In other embodiments, the transgenic plant comprises event Bt11, event 5307 and event MON89034. Is still other embodiments, the transgenic plant comprises event MON810 and MON89034.

According to another embodiment, the invention encompasses a pair of purified antibodies comprising a first antibody and a second antibody that function together in an immunoassay to specifically detect or quantitate a Cry1Ab protein in a biological sample comprising the Cry1Ab protein and a hybrid Cry protein having at least a contiguous 27% of the Cry1Ab protein's amino acid sequence, wherein the first antibody and the second antibody individually are capable of binding to both the Cry1Ab protein and the hybrid Cry protein.

In other embodiments of the invention, the immunoassay is an enzyme-linked immunosorbent assay (ELISA), preferably a sandwich ELISA. In still other embodiments, the first antibody is the coating antibody and the second antibody is the detecting antibody. In still other embodiments, the first and the second antibodies are monoclonal. In yet other embodiments, the first or coating antibody is the monoclonal antibody 87AB1.1, which is available from Romer Labs, Inc (Union, Mo.). In other embodiments, the second or detecting antibody is the monoclonal antibody H04MAb70 produced by the hybridoma cell line H04MAb70 deposited as ATCC Accession No. PTA-122984. In still other embodiments, the coating antibody is 87AB1.1 and the detecting antibody is H04MAb70.

In some embodiments of the invention, the Cry1Ab protein that is specifically detected in an immunoassay of the invention comprises an amino acid sequence represented by SEQ ID NO:1, SEQ ID NO:2 or SEQ ID N:6. In other embodiments, the hybrid Cry protein is eCry3.1Ab (SEQ ID NO:3), Cry1A.105 (SEQ ID NO:4) or Cry1A.105 (SEQ ID NO:5).

In other embodiments of the invention, the biological sample is a transgenic plant sample. In still other embodiments, the transgenic plant is a transgenic corn plant comprising a transgenic event selected from the group consisting of event Bt11, which expresses the Cry1Ab protein of SEQ ID NO:1, event 5307, which expresses the eCry3.1Ab hybrid Cry protein of SEQ ID NO:3, event MON89034, which expresses the Cry1A.105 hybrid Cry protein of SEQ ID NO:5 and event MON810, which expresses the Cry1Ab protein of SEQ ID NO:6. In other embodiments, the transgenic plant comprises event Bt11, event 5307 and event MON89034. Is still other embodiments, the transgenic plant comprises event MON810 and MON89034.

According to yet another embodiment, the invention encompasses a diagnostic kit for detecting a Cry1Ab protein in a biological sample which comprises the Cry1Ab protein and a hybrid Cry protein having at least a contiguous 27% of the Cry1Ab protein's amino acid sequence, wherein the kit comprises a first antibody and a second antibody that function together to specifically detect or quantitate the Cry1Ab protein and that individually are capable of binding both the Cry1Ab protein and the hybrid Cry protein.

In other embodiments of the invention, the immunoassay is an enzyme-linked immunosorbent assay (ELISA), preferably a sandwich ELISA. In still other embodiments, the first antibody is the coating antibody and the second antibody is the detecting antibody. In still other embodiments, the first and the second antibodies are monoclonal. In yet other embodiments, the first or coating antibody is the monoclonal antibody 87AB1.1, which is available from Romer Labs, Inc (Union, Mo.). In other embodiments, the second or detecting antibody is the monoclonal antibody H04MAb70 produced by the hybridoma cell line H04MAb70 deposited as ATCC Accession No. PTA-122984. In still other embodiments, the coating antibody is 87AB1.1 and the detecting antibody is H04MAb70.

In some embodiments of the invention, the Cry1Ab protein that is specifically detected in an immunoassay of the invention comprises an amino acid sequence represented by SEQ ID NO:1, SEQ ID NO:2 or SEQ ID N:6. In other embodiments, the hybrid Cry protein is eCry3.1Ab (SEQ ID NO:3), Cry1A.105 (SEQ ID NO:4) or Cry1A.105 (SEQ ID NO:5).

In other embodiments of the invention, the biological sample is a transgenic plant sample. In still other embodiments, the transgenic plant is a transgenic corn plant comprising a transgenic event selected from the group consisting of event Bt11, which expresses the Cry1Ab protein of SEQ ID NO:1, event 5307, which expresses the eCry3.1Ab hybrid Cry protein of SEQ ID NO:3, event MON89034, which expresses the Cry1A.105 hybrid Cry protein of SEQ ID NO:5 and event MON810, which expresses the Cry1Ab protein of SEQ ID NO:6. In yet further embodiments, the biological sample comprises a Cry1Ab protein from event Bt11 and an eCry3.1Ab hybrid Cry protein from event 5307 and optionally a Cry1A.105 hybrid Cry protein from event MON89034. In still further embodiments, the biological sample comprises a Cry1Ab protein from event MON810 and a Cry1A.105 hybrid Cry protein from event MON89034.

According to another embodiment, the invention encompasses a pair of purified antibodies comprising a first antibody and a second antibody that function together in an immunoassay to specifically detect or quantitate a Cry1Ab protein in a biological sample comprising the Cry1Ab protein and a hybrid Cry protein having at least a contiguous 27% of the Cry1Ab protein's amino acid sequence, wherein the first antibody and the second antibody individually are capable of binding to both the Cry1Ab protein and the hybrid Cry protein.

In other embodiments of the invention, the immunoassay is an enzyme-linked immunosorbent assay (ELISA), preferably a sandwich ELISA. In still other embodiments, the first antibody is the coating antibody and the second antibody is the detecting antibody. In still other embodiments, the first and the second antibodies are monoclonal. In yet other embodiments, the first or coating antibody is the monoclonal antibody 87AB1.1, which is available from Romer Labs, Inc (Union, Mo.). In other embodiments, the second or detecting antibody is the monoclonal antibody H04MAb70 produced by the hybridoma cell line H04MAb70 deposited as ATCC Accession No. PTA-122984. In still other embodiments, the coating antibody is 87AB1.1 and the detecting antibody is H04MAb70.

In some embodiments of the invention, the Cry1Ab protein that is specifically detected in an immunoassay of the invention comprises an amino acid sequence represented by SEQ ID NO:1, SEQ ID NO:2 or SEQ ID N:6. In other embodiments, the hybrid Cry protein is eCry3.1Ab (SEQ ID NO:3), Cry1A.105 (SEQ ID NO:4) or Cry1A.105 (SEQ ID NO:5).

In other embodiments of the invention, the biological sample is a transgenic plant sample. In still other embodiments, the transgenic plant is a transgenic corn plant comprising a transgenic event selected from the group consisting of event Bt11, which expresses the Cry1Ab protein of SEQ ID NO:1, event 5307, which expresses the eCry3.1Ab hybrid Cry protein of SEQ ID NO:3, event MON89034, which expresses the Cry1A.105 hybrid Cry protein of SEQ ID NO:5 and event MON810, which expresses the Cry1Ab protein of SEQ ID NO:6. In further embodiments, the biological sample comprises a Cry1Ab protein from event Bt11 and an eCry3.1Ab hybrid Cry protein from event 5307 and optionally a Cry1A.105 hybrid Cry protein from event MON89034. In still further embodiments, the biological sample comprises a Cry1Ab protein from event MON810 and a Cry1A.105 hybrid Cry protein from event MON89034.

According to another embodiment, the invention encompasses a hybridoma cell line, designated H04MAb70, deposited as ATCC Accession No. PTA-122984, and a hybridoma cell line designated MAb58, deposited as ATCC Accession No. PTA-122985. In other embodiments, the invention encompasses a monoclonal antibody designated HO4MAb70 produced by the HO4MAb hybridoma cell line that binds to both a wild-type Cry1Ab protein and a hybrid Cry protein. In certain other embodiments, the invention encompasses a monoclonal antibody designated MAb58 produced by the hybridoma cell line MAb58 that binds to a hybrid Cry protein.

According to another embodiment, the invention encompasses immunoassay methods to specifically detect or quantitate a Cry1Ab protein in a biological sample comprising the Cry1Ab protein and a hybrid Cry protein having at least a contiguous 27% of the Cry1Ab protein's amino acid sequence. Such methods comprise (a) obtaining a biological sample comprising the Cry1Ab protein and the hybrid Cry protein; and (b) performing an immunoassay on the biological sample, wherein the immunoassay comprises use of a first antibody and a second antibody that individually are capable of binding to the Cry1Ab protein and the hybrid Cry protein but that function together in the immunoassay to specifically detect or quantitate the Cry1Ab protein and not the hybrid Cry protein, resulting in the specific detection or quantitation of the Cry1Ab protein.

In some embodiments, the immunoassay is an enzyme-linked immunosorbent assay (ELISA). In other embodiments, the first antibody is a coating antibody and the second antibody is a detecting antibody. In further embodiments, the coating antibody and the detecting antibody are monoclonal. In still other embodiments, the coating antibody is the monoclonal antibody 87AB1.1 available from Romer Labs, Inc. (Union, Mo.). In yet other embodiments, the detecting antibody is the monoclonal antibody HO4MAb70 produced by the hybridoma cell line deposited as ATCC Accession No. PTA-122984. In other embodiments, the coating antibody is 87AB1.1 and the detecting antibody is HO4MAb70.

In some embodiments of the invention, the Cry1Ab protein is selected from the group consisting of SEQ ID NO:1, SEQ ID NO:2 and SEQ ID NO:6. In other embodiments, the hybrid Cry protein is selected from the group consisting of eCry3.1Ab (SEQ ID NO:3), Cry1A.105 (SEQ ID NO:4) and H04 (SEQ ID NO:5). In still other embodiments, the Cry1Ab protein comprises an amino acid of SEQ ID NO:1 or SEQ ID NO:2 or SEQ ID NO:6 and the hybrid Cry protein is eCry3.1Ab (SEQ ID NO:3) or Cry1A.105 (SEQ ID NO:4) or H04 (SEQ ID NO:5). In other embodiments, the Cry1Ab protein comprises the amino acid sequence of SEQ ID NO:6 and the Cry1A.105 hybrid Cry protein comprises the amino acid of SEQ ID NO:4.

In some other embodiments of the invention, the biological sample tested in the immunoassay is a transgenic plant sample. In other embodiments, the transgenic plant sample is from a transgenic corn plant. In other embodiments, the transgenic corn plant comprises a transgenic corn event selected from the group consisting of event Bt11, event 5307, event MON89034 and event MON810. In still other embodiments, the transgenic corn plant comprises event Bt11, event 5307 and event MON89034. In yet other embodiments, the biological sample comprises a Cry1Ab protein from event Bt11 and an eCry3.1Ab hybrid Cry protein from event 5307 and optionally a Cry1A.105 hybrid Cry protein from event MON89034. In other embodiments, the biological sample comprises a Cry1Ab protein from event MON810 and a Cry1A.105 hybrid Cry protein from event MON89034.

In another embodiment, the invention encompasses an immunoassay method for detecting or quantitating both a Cry1Ab protein and a hybrid Cry protein having at least a contiguous 27% of a Cry1Ab protein's amino acid sequence in a biological sample comprising the hybrid Cry protein and the Cry1Ab protein, the immunoassay method comprising: (a) obtaining a biological sample comprising the hybrid Cry protein and the Cry1Ab protein; (b) contacting the biological sample with a first antibody under conditions effective to allow the formation of a Cry1Ab-first antibody complex but not a hybrid Cry protein-first antibody complex, resulting in a biological sample depleted of the Cry1Ab protein; (c) removing the Cry1Ab-depleted biological sample from contact with the first antibody; (d) contacting the Cry1Ab-depleted biological sample with a second antibody under conditions effective to allow the formation of a hybrid Cry protein-second antibody complex; and (e) detecting or quantitating the hybrid Cry protein in the hybrid Cry protein-second antibody complex.

In some embodiments, the immunoassay is an enzyme-linked immunosorbent assay, wherein the solid surface is plastic well in a microtiter dish. In some embodiments, the Cry1Ab protein is selected from the group consisting of SEQ ID NO:1, SEQ ID NO:2 and SEQ ID NO:6. In other embodiments, the hybrid Cry protein is selected from the group consisting of eCry3.1Ab (SEQ ID NO:3), Cry1A.105 (SEQ ID NO:4) and H04 (SEQ ID NO:5). In still other embodiments, the Cry1Ab protein is SEQ ID NO:1 or SEQ ID NO:2 or SEQ ID NO:6 and the hybrid Cry protein is eCry3.1Ab (SEQ ID NO:3) or Cry1A.105 (SEQ ID NO:4) or H04 (SEQ ID NO:5). In other embodiments, the Cry1Ab protein comprises the amino acid sequence set forth in SEQ ID NO:6 and the Cry1A.105 hybrid Cry protein comprises the amino acid sequence set forth in SEQ ID NO:4. In still other embodiments, the Cry1Ab protein is SEQ ID NO:1 and the hybrid Cry protein is eCry3.1Ab (SEQ ID NO:3) or Cry1A.105 (SEQ ID NO:4).

In other embodiments, the first antibody is 87AB1.1 which is available from Romer Labs, Inc. (Union, Mo.). In still other embodiments, the second antibody is the monoclonal antibody MAb58 produced by the hybridoma cell line deposited as ATCC Accession No. PTA-122985. In yet other embodiments of this aspect, the detecting of step (d) is carried out using a composition comprising a monoclonal antibody capable of binding to the Cry1Ab protein and the hybrid Cry protein. In still further embodiments, the monoclonal antibody is HO4MAb70. In yet other embodiments of this aspect, the detecting step (e) is carried out using a composition comprising a monoclonal antibody or a polyclonal antibody capable of binding to the hybrid Cry protein and the Cry1Ab protein. In further embodiments, the monoclonal antibody is HO4MAb70 or the polyclonal antibody is R-PAb available from Romer Labs, Inc. (Union, Mo.).

According to yet another embodiment, the invention encompasses an immunoassay method to detect or quantitate a hybrid Cry protein having at least a contiguous 27% of a Cry1Ab protein's amino acid sequence in a biological sample comprising the hybrid Cry protein and the Cry1Ab protein. Such methods comprise: (a) obtaining a biological sample comprising the hybrid Cry protein and the Cry1Ab protein; (b) contacting the biological sample with a 87AB1.1 antibody under conditions effective to allow the formation of a Cry1Ab-87AB1.1 complex but not a hybrid Cry protein-87AB1.1 complex, resulting in a biological sample depleted of the Cry1Ab protein; (c) removing the Cry1Ab-depleted biological sample from contact with the 87AB1.1 antibody; (d) contacting the Cry1Ab-depleted biological sample with a second antibody under conditions effective to allow the formation of a hybrid Cry protein-second antibody complex; and (e) detecting or quantitating the hybrid Cry protein in the hybrid Cry protein-second antibody complex.

In some embodiments, the immunoassay is an enzyme-linked immunosorbent assay (ELISA). In some other embodiments of the invention, the Cry1Ab protein is selected from the group consisting of SEQ ID NO:1, SEQ ID NO:2 and SEQ ID NO:6. In other embodiments, the hybrid Cry protein is selected from the group consisting of eCry3.1Ab (SEQ ID NO:3), Cry1A.105 (SEQ ID NO:4) and H04 (SEQ ID NO:5). In still other embodiments, the Cry1Ab protein is SEQ ID NO:1 or SEQ ID NO:2 or SEQ ID NO:6 and the hybrid Cry protein is eCry3.1Ab (SEQ ID NO:3) or Cry1A.105 (SEQ ID NO:4) or H04 (SEQ ID NO:5). In other embodiments, the Cry1Ab protein comprises the amino acid sequence set forth in SEQ ID NO:6 and the Cry1A.105 hybrid Cry protein comprises the amino acid sequence set forth in SEQ ID NO:4.

In some other embodiments of the invention, the biological sample tested in the immunoassay is a transgenic plant sample. In other embodiments, the transgenic plant sample is from a transgenic corn plant. In other embodiments, the transgenic corn plant comprises a transgenic corn event selected from the group consisting of event Bt11, event 5307, event MON89034 and event MON810. In still other embodiments, the transgenic corn plant comprises event Bt11, event 5307 and event MON89034. In yet other embodiments, the biological sample comprises a Cry1Ab protein from event Bt11 and an eCry3.1Ab hybrid Cry protein from event 5307 and optionally a Cry1A.105 hybrid Cry protein from event MON89034. In other embodiments, the biological sample comprises a Cry1Ab protein from event MON810 and a Cry1A.105 hybrid Cry protein from event MON89034.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., Molecular Cloning: A Laboratory Manual, 3d Ed., Cold Spring Harbor, N.Y.: Cold Spring Harbor Laboratory Press (2001); by T. J. Silhavy, M. L. Berman, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, New York, John Wiley and Sons Inc., (1988), Reiter, et al., Methods in *Arabidopsis* Research, World Scientific Press (1992), and Schultz et al., Plant Molecular Biology Manual, Kluwer Academic Publishers (1998).

Example 1—Screening Antibody Pairs

This example describes antibody embodiments of the invention and the identification of functional antibody pairs. Antibody pairs were tested for their ability to specifically detect a Cry1Ab protein (SEQ ID NO:1) when in the presence of an eCry3.1Ab protein (SEQ ID NO:3) or a Cry1A.105 protein (SEQ ID NO:4) or both, which are hybrid Cry proteins having at least a contiguous 27% of the Cry1Ab protein's amino acid sequence as shown in FIGS. 2 and 3, respectively. Antibodies tested and their sources are listed in Table 1.

TABLE 1

| Antibodies Tested for Combination Functionality. | |
|---|---|
| H04 MAb70 | Monoclonal antibody raised against a hybrid Cry protein antigen comprising domain I and II of a Cry1Ab, domain III or a Cry1C and a protoxin tail from a Cry1Ab (See FIG. 1). Hybridoma cell line deposited as ATCC PTA-122984. |
| MAb58 | Monoclonal antibody raised against a full-length wild-type Cry1Ab protein antigen. Hybridoma cell line deposited as ATCC PTA-122985. |
| PAb713 | Polyclonal antibody available from Romer Labs, Inc (Union, MO) raised against a wild-type Cry1Ab protein antigen. |
| 87AB1.1 | Monoclonal antibody available from Romer Labs, Inc. (Union, MO) raised against a wild-type Cry1Ab protein antigen. |
| Cry1Ab/Cry1Ac Con | Polyclonal antibody conjugate available from EnviroLogix (Portland, ME) raised against a wild-type Cry1Ab/Cry1Ac protein antigen. |

Antibody pairs are tested in a standard sandwich ELISA. Wells of a 96-well plate are coated with a first antibody (coating antibody), typically by incubating over night at approximately 2°-8° C. Plates are then washed before adding a sample comprising a Cry1Ab protein, a Cry1A.105 protein and an eCry3.1Ab protein. Wells are then thoroughly mixed by moving the plate for approximately 20-30 sec, after which the plates are incubated at ambient temperature for approximately 1 to 2 hours. Optionally the plate may be shaken on an orbital shaker at approximately 200 rpm during the incubation period. After incubation, sample liquid is removed from the wells and the wells are washed completely 2-3× with a wash buffer. After washing, a second antibody (detection antibody) labelled with a detection enzyme is added to the wells. The plates are incubated at ambient temperature for another approximately 1 to 2 hours. After incubation the plates are washed completely with wash buffer. Approximately 100 µl of substrate is then added to each well and the plates incubated at ambient temperature for approximately 15-30 minutes. Plates are inspected for substrate color development and scored as positive, "+" or negative "−" for each of the three proteins of interest.

Surprisingly, the results, shown in Table 2, demonstrate that when individual antibodies that are capable of binding all three proteins, i.e. Cry1Ab, eCry3.1Ab and Cry1A.105, are used in pairs, the pairs function collectively to be selective for either Cry1Ab or a hybrid Cry protein. This is even more surprising for individual antibodies that are raised against a wild-type Cry1Ab protein like 87AB1.1 and MAb58 or for an antibody raised against a hybrid protein made up of almost 70% of wild-type Cry1Ab amino acid sequence like H04MAb70 (See FIGS. 1 and 4). Alone such an antibody cannot differentiate between Cry1Ab, Cry1A.105 or eCry3.1Ab. However, in combination with another antibody, the first or the second antibody is now made selective for just Cry1Ab. For example, these results surprisingly demonstrate that an immunoassay of a complex biological sample comprising Cry1Ab, Cry1A.105 and eCry3.1Ab using a pair of antibodies, where the first antibody is 87AB1.1, a monoclonal antibody raised against a wild-type Cry1Ab protein that is capable of binding both a Cry1Ab protein and an eCry3.1Ab protein, which is a hybrid Cry protein having at least a contiguous 27% of the Cry1Ab protein's amino acid sequence, and the second antibody is H04MAb70, a monoclonal antibody raised against a hybrid Cry protein having at least one contiguous 39% of a Cry1Ab protein's amino acid sequence and capable of binding Cry1Ab, Cry1A.105 and eCry3.1Ab, specifically detects the Cry1Ab protein. Thus when used in combination, the functionality of the first antibody and the second antibody is markedly different than either of the antibodies alone.

The results also surprisingly demonstrate that an immunoassay of a complex biological sample comprising Cry1Ab, Cry1A.105 and eCry3.1Ab using a pair of antibodies, where the first antibody is MAb58, a monoclonal antibody raised against a wild-type Cry1Ab protein, and the second antibody is H04MAb70, is selective for the Cry1A.105 protein. Thus, when used in combination, the functionality of the first antibody, MAb58, and the second antibody, H04MAb70, is markedly different than either antibody alone.

TABLE 2

Results of the Antibody Combination Tests.

| Coating Antibody | Detection Antibody | Protein Detected in ELISA | | |
|---|---|---|---|---|
| | | Cry1Ab | Cry1A.105 | eCry3.1Ab |
| HO4 MAb70 | PAb713 | + | + | + |
| PAb713 | HO4 MAb70 | + | − | + |
| 87Ab1.1 | PAb713 | + | − | + |
| PAb713 | MAb 87Ab1.1 | + | + | − |
| Mab58 | PAb713 | − | + | − |
| Mab58 | HO4 MAb70 | − | + | − |
| 87Ab1.1 | HO4 MAb70 | + | − | − |
| Cry1Ab-Ac Con | Cry1Ab-Ac Con | + | − | + |
| PAb713 | Cry1Ab-Ac Con | + | + | + |

Example 2—Quantitative Analysis for Cry1Ab

This example describes a procedure for specific detection and quantification of a Cry1Ab protein in a complex biological sample, for example a transgenic plant sample, comprising the Cry1Ab protein and two hybrid Cry proteins having at least a contiguous 27% of the Cry1Ab protein's amino acid sequence by enzyme linked immunosorbent assay (ELISA).

A 96-well Nunc Maxisorp plate is coated with 100 µl per well of a solution comprising the monoclonal antibody 87AB1.1, available from Romer Labs, Inc (Union, Mo.). Plates are covered with a 96-well plate lid and incubated minimally overnight at approximately 2° C. to 8° C. If the plates are allowed to incubate longer than overnight, cover the plate with an adhesive plate sealer to prevent evaporation and contamination of the wells. Wash the plates at least three times with 1× phosphate buffered saline with Tween® 20 (PBST) wash buffer (§ 11.2.3) using approximately 300 µl/well. As a blocking step, add approximately 200 µl of Superblock® per well. Incubate the plates at room temperature while shaking at approximately 400 rpm for at least 30 minutes. Wash the plates at least three times with 1×PBST wash buffer using approximately 300 µl/well.

Dilutions: Sample extracts are diluted in 1×PBST (137 mM sodium chloride, 2.7 mM potassium chloride, 10 mM sodium phosphate dibasic, 1.8 mM potassium phosphate monobasic and 0.05% Tween® 20) with 1% bovine serum albumin (BSA) buffer. At least two dilutions of each sample extract should be analyzed to obtain multiple concentrations across the quantitative range of the standard curve. Sample extracts should be mixed thoroughly before use. Prepare a minimum volume of the initial dilution so that sufficient volume is available to create subsequent dilutions for accurate duplicate analysis (100 µl each). Increase the volume of the initial dilution appropriately if samples will be analyzed in triplicate. Mix dilutions by pipetting up and down several times. For example, a 1:20 dilution would be made up as follows: 760 µl of 1×PBST with 1% BSA buffer+40 µl of extract=800 µl (total volume). Subsequent 1:2 dilutions can be made from the first dilution. The minimum dilution factor for all matrices is located in Table 1.

Preparation of Standard Curve: Prepare the standard curve containing the following concentrations of Cry1Ab in 1×PBST with 1% BSA buffer: 12.5, 6.25, 3.13, 1.56, 0.781, 0.391, 0.195 and 0.098 ng/ml. See Table 3 for example dilution series. Solutions may be prepared in microtubes to facilitate efficient loading of ELISA plates with standard curve solution.

TABLE 3

Cry1Ab Standard Curve Preparation (provides standard solutions for one plate; adjust volumes as necessary for additional plates)

| Concentration of Previous Solution (ng/ml) | Dilution of Previous Solution (1:X) | Volume of Previous Solution (µl) | PBST + 1% BSA Buffer Volume (µl) | Final Standard Concentration (ng/ml) | Final Volume (µl) |
|---|---|---|---|---|---|
| 82000* | 82 | 10 | 810 | 1000 | 810 |
| 1000 | 80 | 10 | 790 | 12.5 | 400 |
| 12.5 | 2 | 400 | 400 | 6.25 | 400 |
| 6.25 | 2 | 400 | 400 | 3.13 | 400 |
| 3.13 | 2 | 400 | 400 | 1.56 | 400 |
| 1.56 | 2 | 400 | 400 | 0.781 | 400 |
| 0.781 | 2 | 400 | 400 | 0.391 | 400 |
| 0.391 | 2 | 400 | 400 | 0.195 | 400 |
| 0.195 | 2 | 400 | 400 | 0.098 | 800 |

Loading the Plate: Sample extract dilutions should be prepared so that the plate can be loaded quickly and efficiently to minimize variation in incubation time between the first and last samples loaded. Place 100 µl of the standards in the wells in triplicate, then place 100 µl of samples and PACS into the wells in no less than duplicate. Cover the plate and incubate at room temperature for at least one hour while shaking at approximately 400 rpm.

Wash the plate at least five times with 1×PBST buffer with approximately 300 µl/well. Add 100 µl/well of the appropriately diluted H04Mab 70-HRP antibody. Cover the plate and incubate at room temperature for at least one hour while shaking at approximately 400 rpm. Wash the plate at least five times with 1×PBST buffer with approximately 300 µl/well. Add 100 µl/well of the TMB substrate solution (1 tablet TMB, 10 ml citrate phosphate buffer and 2 µl hydrogen peroxide) using an appropriate multichannel device to each well of the plate(s) and incubate the plate at room temperature, in the dark, while shaking at approximately 400 rpm until the appropriate color development has been achieved (approximately 15 minutes). Stop the reaction by adding 50 µl/well of 3 M sulfuric acid. Read the absorbance of the wells at a wavelength of 450 nm using a SPECTRAmax Pro plate reader. Other plate readers may be used if necessary.

Interpretation of Results: Data are analyzed using Soft-Max® Pro software or equivalent.

Standard Curve: A 4-parameter logistic algorithm is used to fit the standard curve. For each standard curve dilution, the coefficient of variation (CV) of the optical density (OD) values must be ≤20%. A minimum of two replicates is required for analysis; one of the triplicate OD values may be omitted as needed to yield an acceptable CV value. For documentation purposes, this is indicated on the data printout by both drawing a single line through the omitted data point and writing the corrected mean in the "mean" column or by masking the well in the software program used for analysis. If the CV of the OD values of duplicate standards is >20%, then the ELISA must be repeated. The mean back calculated concentration (MBCC) value must be within 70%-120% of the nominal concentration for each standard point within the quantitative range of the assay. One of the triplicate OD values may be omitted as needed to yield an acceptable criterion, however a minimum of two replicates is required for analysis; See § 9.2.2 for documentation guidelines. The quantitative range of the Cry1Ab standard curve is 0.195 ng/ml to 12.5 ng/ml. The coefficient of determination ($R^2$) must be ≥0.990.

Positive Assay Control Sample: For each PACS dilution, the CV between replicate concentrations must be ≤20%. To be a valid PACS dilution, a minimum of two replicates is required for analysis. If assayed in triplicate, one of the triplicate concentrations may be omitted as needed to yield an acceptable CV value. To calculate the mean PACS concentration, multiply the measured concentration (ng/ml) by the corresponding dilution factor to determine the calculated concentration for each dilution in µg/ml. Average all calculated concentrations that fall within the accurate range of the assay to determine the overall Cry1Ab PACS concentration in µg/ml. The CV of the calculated concentration among PACS dilutions must be ≤20%. If the CV of the calculated concentration among PACS dilutions is >20%, and/or the mean PACS concentration is outside the specification range, the ELISA plate data is invalidated and all samples on that plate will be reanalyzed in another ELISA session.

Test Samples: For each sample dilution, the CV between replicate concentrations must be ≤20%. To be a valid sample dilution, a minimum of two replicates is required for analysis. If assayed in triplicate, one of the triplicate concentrations may be omitted as needed to yield an acceptable CV value. The mean measured concentration obtained by ELISA for each sample dilution must lie within the quantitative range of the ELISA (Table 2). To calculate the sample concentration, multiply each measured sample protein concentration that is within the quantitative range of the ELISA by the corresponding dilution factor. Average the results from at least two sample dilutions to determine the overall sample concentration, unless the sample dilution at the minimum dilution factor for a given matrix is the only result within the quantitative range. The CV of the calculated concentration among sample dilutions must be ≤20%. If the CV among sample dilutions is >20% and more than two dilutions are used to calculate the concentration, one outlying dilution may be omitted and the mean concentration recalculated from the remaining dilutions.

Results: Samples of leaf, kernel and root tissue from a triple stack (three events) transgenic corn plant comprising the transgenic corn events Bt11 expressing Cry1Ab, 5307 expressing eCry3.1Ab and MON89034 expressing Cry1A.105 were tested using the immunoassay described above to quantitate specifically the Cry1Ab protein concentration in the samples. Four different samples for each tissue were prepared and 3 replicates from each sample were assayed. The concentration of Cry1Ab protein in transgenic corn comprising the Bt11 event alone has been reported to range from approximately 12-154 µg/g dry weight (DW) in leaves and approximately 9-22 µg/gDW in roots (September 2010. US Environmental Protection Agency Biopesticides Registration Action Document. Cry1Ab and Cry1F *Bacillus thuringiensis* (Bt) Corn Plant-Incorporated Protectants). Results of the immunoassay of a stacked product, shown in Table 4, demonstrate that the concentration of Cry1Ab in the stacked product is comparable to the Cry1Ab concentration in Bt11 alone, indicating that the immunoassay can specifically detect and quantitate Cry1Ab in the presence of one or more hybrid Cry proteins having at a contiguous 27% of the Cry1Ab protein's amino acid sequence.

TABLE 4

Quantitation of Cry1Ab in a Sample Comprising Cry1Ab, eCry3.1Ab and Cry1A.105.

| Sample | Mean Cry1Ab Concentration (µg/gDW) | Standard Deviation (SD) | Range (−2 to +2 SD) |
|---|---|---|---|
| Leaf | 70.79 | 5.34 | 60.12-81.47 |
| Root | 18.69 | 1.85 | 14.99-22.38 |
| Kernel | 3.98 | 0.49 | 3.00-4.97 |

Example 3—Quantitation of a Hybrid Cry Protein or Both a Cry1Ab Protein and Hybrid Cry Protein in Same Immunoassay Based on the discovery that certain antibody pairs have markedly different function than either antibody when used alone, a serial immunoassay was developed that allows for detection or quantitation of both a wild-type Cry1Ab and a hybrid Cry protein having a contiguous 27% of the Cry1Ab protein's amino acid sequence in the same immunoassay. Briefly the method comprises coating a first 96-well microtiter plate with the 87AB1.1 monoclonal antibody, which when used in a pair of antibodies selectively detects a wild-type Cry1Ab protein in a mixture of Cry1Ab and a hybrid Cry protein and a second 96-well microtiter plate with a MAb58 antibody. Contacting a biological sample from a transgenic plant comprising a Cry1Ab protein from event Bt11, a hybrid Cry protein, eCry3.1Ab, from event 5307 and a hybrid Cry protein, Cry1A.105, from event MON89034 with the 87AB1.1 antibody under conditions effective to allow the formation of a Cry1Ab-87AB1.1 complex but not a hybrid Cry protein-87AB1.1 complex as described above in Example 2. This results in a biological sample in the microtiter wells that is depleted of the Cry1Ab protein. Next remove the Cry1Ab-depleted biological sample from the first microtiter dish and transfer to the second microtiter dish, contacting the Cry1Ab-depleted biological sample with the MAb58 antibody under conditions effective to allow the formation of a Cry1A.105-MAb58 complex. Next add the appropriate dilution of a solution comprising a H04MAb70-HRP labelled antibody or a PAb713-HRP labelled antibody. Incubated under conditions effective to allow the formation of a Cry1A.105-H04MAb70 or Cry1A.105-PAb713 complex. Then add a substrate to detect or quantitate the Cry1A.105 protein by comparing to a Cry1A.105 standard curve.

Optionally, the Cry1Ab protein on the first microtiter plate can also be detected or quantitated in the same immunoassay by following the procedure described in Example 2.

It should be understood that the examples and embodiments described herein are for illustrative purposes only and that various modifications or changes in light thereof will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

SEQUENCE LISTING

<160> NUMBER OF SEQ ID NOS: 6

<210> SEQ ID NO 1
<211> LENGTH: 614
<212> TYPE: PRT
<213> ORGANISM: Bacillus thuringiensis

<400> SEQUENCE: 1

```
Met Asp Asn Asn Pro Asn Ile Asn Glu Cys Ile Pro Tyr Asn Cys Leu
1

```
Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
                580                 585                 590

Ser Gly Asn Glu Val Tyr Ile Asp Arg Ile Glu Phe Val Pro Ala Glu
            595                 600                 605

Val Thr Phe Glu Ala Glu
    610

<210> SEQ ID NO 2
<211> LENGTH: 1155
<212> TYPE: PRT
<213> ORGANISM: Bacillus thuringiensis

<400> SEQUENCE: 2

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
        50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125
```

-continued

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
    290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
            500                 505                 510

Val Asn Ile Thr Ala Pro Leu Ser Gln Arg Tyr Arg Val Arg Ile Arg
        515                 520                 525

Tyr Ala Ser Thr Thr Asn Leu Gln Phe His Thr Ser Ile Asp Gly Arg
    530                 535                 540

-continued

```
Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
        595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
            660                 665                 670

His Ala Lys Arg Leu Ser Asp Glu Arg Asn Leu Leu Gln Asp Pro Asn
        675                 680                 685

Phe Arg Gly Ile Asn Arg Gln Leu Asp Arg Gly Trp Arg Gly Ser Thr
    690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Pro Thr Tyr Leu Tyr Gln
                725                 730                 735

Lys Ile Asp Glu Ser Lys Leu Lys Ala Tyr Thr Arg Tyr Gln Leu Arg
            740                 745                 750

Gly Tyr Ile Glu Asp Ser Gln Asp Leu Glu Ile Tyr Leu Ile Arg Tyr
        755                 760                 765

Asn Ala Lys His Glu Thr Val Asn Val Pro Gly Thr Gly Ser Leu Trp
    770                 775                 780

Pro Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
            820                 825                 830

Arg Leu Gly Asn Leu Glu Phe Leu Glu Lys Pro Leu Val Gly Glu
        835                 840                 845

Ala Leu Ala Arg Val Lys Arg Ala Glu Lys Lys Trp Arg Asp Lys Arg
    850                 855                 860

Glu Lys Leu Glu Trp Glu Thr Asn Ile Val Tyr Lys Glu Ala Lys Glu
865                 870                 875                 880

Ser Val Asp Ala Leu Phe Val Asn Ser Gln Tyr Asp Arg Leu Gln Ala
                885                 890                 895

Asp Thr Asn Ile Ala Met Ile His Ala Ala Asp Lys Arg Val His Ser
            900                 905                 910

Ile Arg Glu Ala Tyr Leu Pro Glu Leu Ser Val Ile Pro Gly Val Asn
        915                 920                 925

Ala Ala Ile Phe Glu Glu Leu Glu Gly Arg Ile Phe Thr Ala Phe Ser
    930                 935                 940

Leu Tyr Asp Ala Arg Asn Val Ile Lys Asn Gly Asp Phe Asn Asn Gly
945                 950                 955                 960

Leu Ser Cys Trp Asn Val Lys Gly His Val Asp Val Glu Glu Gln Asn
```

```
                     965                 970                 975
Asn His Arg Ser Val Leu Val Pro Glu Trp Glu Ala Glu Val Ser
                980                 985                 990

Gln Glu Val Arg Val Cys Pro Gly Arg Gly Tyr Ile Leu Arg Val Thr
        995                 1000                1005

Ala Tyr Lys Glu Gly Tyr Gly Glu Gly Cys Val Thr Ile His Glu
    1010                1015                1020

Ile Glu Asn Asn Thr Asp Glu Leu Lys Phe Ser Asn Cys Val Glu
    1025                1030                1035

Glu Glu Val Tyr Pro Asn Asn Thr Val Thr Cys Asn Asp Tyr Thr
    1040                1045                1050

Ala Thr Gln Glu Glu Tyr Glu Gly Thr Tyr Thr Ser Arg Asn Arg
    1055                1060                1065

Gly Tyr Asp Gly Ala Tyr Glu Ser Asn Ser Ser Val Pro Ala Asp
    1070                1075                1080

Tyr Ala Ser Ala Tyr Glu Glu Lys Ala Tyr Thr Asp Gly Arg Arg
    1085                1090                1095

Asp Asn Pro Cys Glu Ser Asn Arg Gly Tyr Gly Asp Tyr Thr Pro
    1100                1105                1110

Leu Pro Ala Gly Tyr Val Thr Lys Glu Leu Glu Tyr Phe Pro Glu
    1115                1120                1125

Thr Asp Lys Val Trp Ile Glu Ile Gly Glu Thr Glu Gly Thr Phe
    1130                1135                1140

Ile Val Asp Ser Val Glu Leu Leu Leu Met Glu Glu
    1145                1150                1155

<210> SEQ ID NO 3
<211> LENGTH: 653
<212> TYPE: PRT
<213> ORGANISM: Artificial Sequence
<220> FEATURE:
<223> OTHER INFORMATION: Hybrid Cry protein comprising a portion of
      Cry3A and Cry1Ab.

<400> SEQUENCE: 3

Met Thr Ser Asn Gly Arg Gln Cys Ala Gly Ile Arg Pro Tyr Asp Gly
1               5                   10                  15

Arg Gln Gln His Arg Gly Leu Asp Ser Ser Thr Thr Lys Asp Val Ile
            20                  25                  30

Gln Lys Gly Ile Ser Val Val Gly Asp Leu Leu Gly Val Val Gly Phe
        35                  40                  45

Pro Phe Gly Gly Ala Leu Val Ser Phe Tyr Thr Asn Phe Leu Asn Thr
    50                  55                  60

Ile Trp Pro Ser Glu Asp Pro Trp Lys Ala Phe Met Glu Gln Val Glu
65                  70                  75                  80

Ala Leu Met Asp Gln Lys Ile Ala Asp Tyr Ala Lys Asn Lys Ala Leu
                85                  90                  95

Ala Glu Leu Gln Gly Leu Gln Asn Asn Val Glu Asp Tyr Val Ser Ala
            100                 105                 110

Leu Ser Ser Trp Gln Lys Asn Pro Ala Ala Pro Phe Arg Asn Pro His
        115                 120                 125

Ser Gln Gly Arg Ile Arg Glu Leu Phe Ser Gln Ala Glu Ser His Phe
    130                 135                 140

Arg Asn Ser Met Pro Ser Phe Ala Ile Ser Gly Tyr Glu Val Leu Phe
145                 150                 155                 160
```

```
Leu Thr Thr Tyr Ala Gln Ala Ala Asn Thr His Leu Phe Leu Leu Lys
                165                 170                 175

Asp Ala Gln Ile Tyr Gly Glu Glu Trp Gly Tyr Glu Lys Glu Asp Ile
            180                 185                 190

Ala Glu Phe Tyr Lys Arg Gln Leu Lys Leu Thr Gln Glu Tyr Thr Asp
            195                 200                 205

His Cys Val Lys Trp Tyr Asn Val Gly Leu Asp Lys Leu Arg Gly Ser
            210                 215                 220

Ser Tyr Glu Ser Trp Val Asn Phe Asn Arg Tyr Arg Arg Glu Met Thr
225                 230                 235                 240

Leu Thr Val Leu Asp Leu Ile Ala Leu Phe Pro Leu Tyr Asp Val Arg
                245                 250                 255

Leu Tyr Pro Lys Glu Val Lys Thr Glu Leu Thr Arg Asp Val Leu Thr
                260                 265                 270

Asp Pro Ile Val Gly Val Asn Asn Leu Arg Gly Tyr Gly Thr Thr Phe
            275                 280                 285

Ser Asn Ile Glu Asn Tyr Ile Arg Lys Pro His Leu Phe Asp Tyr Leu
            290                 295                 300

His Arg Ile Gln Phe His Thr Arg Phe Gln Pro Gly Tyr Tyr Gly Asn
305                 310                 315                 320

Asp Ser Phe Asn Tyr Trp Ser Gly Asn Tyr Val Ser Thr Arg Pro Ser
                325                 330                 335

Ile Gly Ser Asn Asp Ile Ile Thr Ser Pro Phe Tyr Gly Asn Lys Ser
                340                 345                 350

Ser Glu Pro Val Gln Asn Leu Glu Phe Asn Gly Glu Lys Val Tyr Arg
            355                 360                 365

Ala Val Ala Asn Thr Asn Leu Ala Val Trp Pro Ser Ala Val Tyr Ser
            370                 375                 380

Gly Val Thr Lys Val Glu Phe Ser Gln Tyr Asn Asp Gln Thr Asp Glu
385                 390                 395                 400

Ala Ser Thr Gln Thr Tyr Asp Ser Lys Arg Asn Val Gly Ala Val Ser
                405                 410                 415

Trp Asp Ser Ile Asp Gln Leu Pro Pro Glu Thr Thr Asp Glu Pro Leu
                420                 425                 430

Glu Lys Gly Tyr Ser His Gln Leu Asn Tyr Val Met Cys Phe Leu Met
            435                 440                 445

Gln Gly Ser Arg Gly Thr Ile Pro Val Leu Thr Trp Thr His Lys Ser
            450                 455                 460

Val Asp Phe Phe Asn Met Ile Asp Ser Lys Lys Ile Thr Gln Leu Pro
465                 470                 475                 480

Leu Thr Lys Ser Thr Asn Leu Gly Ser Gly Thr Ser Val Val Lys Gly
                485                 490                 495

Pro Gly Phe Thr Gly Gly Asp Ile Leu Arg Arg Thr Ser Pro Gly Gln
            500                 505                 510

Ile Ser Thr Leu Arg Val Asn Ile Thr Ala Pro Leu Ser Gln Arg Tyr
            515                 520                 525

Arg Val Arg Ile Arg Tyr Ala Ser Thr Thr Asn Leu Gln Phe His Thr
530                 535                 540

Ser Ile Asp Gly Arg Pro Ile Asn Gln Gly Asn Phe Ser Ala Thr Met
545                 550                 555                 560

Ser Ser Gly Ser Asn Leu Gln Ser Gly Ser Phe Arg Thr Val Gly Phe
                565                 570                 575

Thr Thr Pro Phe Asn Phe Ser Asn Gly Ser Ser Val Phe Thr Leu Ser
```

```
            580                 585                 590

Ala His Val Phe Asn Ser Gly Asn Glu Val Tyr Ile Asp Arg Ile Glu
        595                 600                 605

Phe Val Pro Ala Glu Val Thr Phe Glu Ala Glu Tyr Asp Leu Glu Arg
    610                 615                 620

Ala Gln Lys Ala Val Asn Glu Leu Phe Thr Ser Ser Asn Gln Ile Gly
625                 630                 635                 640

Leu Lys Thr Asp Val Thr Asp Tyr His Ile Asp Gln Val
                645                 650

<210> SEQ ID NO 4
<211> LENGTH: 1177
<212> TYPE: PRT
<213> ORGANISM: Artificial Sequence
<220> FEATURE:
<223> OTHER INFORMATION: Hybrid Cry protein made with a portion of
      Cry1Ab + Cry1F + Cry1Ac.

<400> SEQUENCE: 4

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

```
Gly Ser Ile Arg Ser Pro His Leu Met Asp Ile Leu Asn Ser Ile Thr
    290                 295                 300
Ile Tyr Thr Asp Ala His Arg Gly Glu Tyr Tyr Trp Ser Gly His Gln
305                 310                 315                 320
Ile Met Ala Ser Pro Val Gly Phe Ser Gly Pro Glu Phe Thr Phe Pro
                325                 330                 335
Leu Tyr Gly Thr Met Gly Asn Ala Ala Pro Gln Gln Arg Ile Val Ala
                340                 345                 350
Gln Leu Gly Gln Gly Val Tyr Arg Thr Leu Ser Ser Thr Leu Tyr Arg
            355                 360                 365
Arg Pro Phe Asn Ile Gly Ile Asn Asn Gln Gln Leu Ser Val Leu Asp
370                 375                 380
Gly Thr Glu Phe Ala Tyr Gly Thr Ser Ser Asn Leu Pro Ser Ala Val
385                 390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
                420                 425                 430
Val Ser Met Phe Arg Ser Gly Phe Ser Asn Ser Ser Val Ser Ile Ile
            435                 440                 445
Arg Ala Pro Met Phe Ser Trp Ile His Arg Ser Ala Glu Phe Asn Asn
450                 455                 460
Ile Ile Ala Ser Asp Ser Ile Thr Gln Ile Pro Leu Val Lys Ala His
465                 470                 475                 480
Thr Leu Gln Ser Gly Thr Thr Val Val Arg Gly Pro Gly Phe Thr Gly
                485                 490                 495
Gly Asp Ile Leu Arg Arg Thr Ser Gly Gly Pro Phe Ala Tyr Thr Ile
                500                 505                 510
Val Asn Ile Asn Gly Gln Leu Pro Gln Arg Tyr Arg Ala Arg Ile Arg
            515                 520                 525
Tyr Ala Ser Thr Thr Asn Leu Arg Ile Tyr Val Thr Val Ala Gly Glu
530                 535                 540
Arg Ile Phe Ala Gly Gln Phe Asn Lys Thr Met Asp Thr Gly Asp Pro
545                 550                 555                 560
Leu Thr Phe Gln Ser Phe Ser Tyr Ala Thr Ile Asn Thr Ala Phe Thr
                565                 570                 575
Phe Pro Met Ser Gln Ser Ser Phe Thr Val Gly Ala Asp Thr Phe Ser
                580                 585                 590
Ser Gly Asn Glu Val Tyr Ile Asp Arg Phe Glu Leu Ile Pro Val Thr
            595                 600                 605
Ala Thr Leu Glu Ala Glu Tyr Asn Leu Glu Arg Ala Gln Lys Ala Val
610                 615                 620
Asn Ala Leu Phe Thr Ser Thr Asn Gln Leu Gly Leu Lys Thr Asn Val
625                 630                 635                 640
Thr Asp Tyr His Ile Asp Gln Val Ser Asn Leu Val Thr Tyr Leu Ser
                645                 650                 655
Asp Glu Phe Cys Leu Asp Glu Lys Arg Glu Leu Ser Glu Lys Val Lys
                660                 665                 670
His Ala Lys Arg Leu Ser Asp Glu Arg Asn Leu Leu Gln Asp Ser Asn
            675                 680                 685
Phe Lys Asp Ile Asn Arg Gln Pro Glu Arg Gly Trp Gly Gly Ser Thr
690                 695                 700
Gly Ile Thr Ile Gln Gly Gly Asp Asp Val Phe Lys Glu Asn Tyr Val
```

-continued

```
           705                 710                 715                 720
Thr Leu Ser Gly Thr Phe Asp Glu Cys Tyr Pro Thr Tyr Leu Tyr Gln
                    725                 730                 735
Lys Ile Asp Glu Ser Lys Leu Lys Ala Phe Thr Arg Tyr Gln Leu Arg
                    740                 745                 750
Gly Tyr Ile Glu Asp Ser Gln Asp Leu Glu Ile Tyr Ser Ile Arg Tyr
                    755                 760                 765
Asn Ala Lys His Glu Thr Val Asn Val Pro Gly Thr Gly Ser Leu Trp
                    770                 775                 780
Pro Leu Ser Ala Gln Ser Pro Ile Gly Lys Cys Gly Glu Pro Asn Arg
785                 790                 795                 800
Cys Ala Pro His Leu Glu Trp Asn Pro Asp Leu Asp Cys Ser Cys Arg
                    805                 810                 815
Asp Gly Glu Lys Cys Ala His His Ser His His Phe Ser Leu Asp Ile
                    820                 825                 830
Asp Val Gly Cys Thr Asp Leu Asn Glu Asp Leu Gly Val Trp Val Ile
                    835                 840                 845
Phe Lys Ile Lys Thr Gln Asp Gly His Ala Arg Leu Gly Asn Leu Glu
850                 855                 860
Phe Leu Glu Glu Lys Pro Leu Val Gly Glu Ala Leu Ala Arg Val Lys
865                 870                 875                 880
Arg Ala Glu Lys Lys Trp Arg Asp Lys Arg Glu Lys Leu Glu Trp Glu
                    885                 890                 895
Thr Asn Ile Val Tyr Lys Glu Ala Lys Glu Ser Val Asp Ala Leu Phe
                    900                 905                 910
Val Asn Ser Gln Tyr Asp Gln Leu Gln Ala Asp Thr Asn Ile Ala Met
                    915                 920                 925
Ile His Ala Ala Asp Lys Arg Val His Ser Ile Arg Glu Ala Tyr Leu
                    930                 935                 940
Pro Glu Leu Ser Val Ile Pro Gly Val Asn Ala Ala Ile Phe Glu Glu
945                 950                 955                 960
Leu Glu Gly Arg Ile Phe Thr Ala Phe Ser Leu Tyr Asp Ala Arg Asn
                    965                 970                 975
Val Ile Lys Asn Gly Asp Phe Asn Asn Gly Leu Ser Cys Trp Asn Val
                    980                 985                 990
Lys Gly His Val Asp Val Glu Glu  Gln Asn Asn Gln Arg  Ser Val Leu
                    995                1000                1005
Val Val  Pro Glu Trp Glu Ala  Glu Val Ser Gln Glu  Val Arg Val
        1010                1015                1020
Cys Pro  Gly Arg Gly Tyr Ile  Leu Arg Val Thr Ala  Tyr Lys Glu
        1025                1030                1035
Gly Tyr  Gly Glu Gly Cys Val  Thr Ile His Glu Ile  Glu Asn Asn
        1040                1045                1050
Thr Asp  Glu Leu Lys Phe Ser  Asn Cys Val Glu Glu  Glu Ile Tyr
        1055                1060                1065
Pro Asn  Asn Thr Val Thr Cys  Asn Asp Tyr Thr Val  Asn Gln Glu
        1070                1075                1080
Glu Tyr  Gly Gly Ala Tyr Thr  Ser Arg Asn Arg Gly  Tyr Asn Glu
        1085                1090                1095
Ala Pro  Ser Val Pro Ala Asp  Tyr Ala Ser Val Tyr  Glu Glu Lys
        1100                1105                1110
Ser Tyr  Thr Asp Gly Arg Arg  Glu Asn Pro Cys Glu  Phe Asn Arg
        1115                1120                1125
```

```
Gly Tyr Arg Asp Tyr Thr Pro Leu Pro Val Gly Tyr Val Thr Lys
            1130                1135                1140

Glu Leu Glu Tyr Phe Pro Glu Thr Asp Lys Val Trp Ile Glu Ile
        1145                1150                1155

Gly Glu Thr Glu Gly Thr Phe Ile Val Asp Ser Val Glu Leu Leu
    1160                1165                1170

Leu Met Glu Glu
        1175

<210> SEQ ID NO 5
<211> LENGTH: 1193
<212> TYPE: PRT
<213> ORGANISM: Artificial Sequence
<220> FEATURE:
<223> OTHER INFORMATION: Hybrid Cry protein made with a portion of
      Cry1Ab + Cry1C + Cry1Ab

<400> SEQU

```
              290                 295                 300
Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Thr Leu Thr Asn
        450                 455                 460

Thr Ile Asp Pro Glu Arg Ile Asn Gln Ile Pro Leu Val Lys Gly Phe
465                 470                 475                 480

Arg Val Trp Gly Gly Thr Ser Val Ile Thr Gly Pro Gly Phe Thr Gly
                485                 490                 495

Gly Asp Ile Leu Arg Arg Asn Thr Phe Gly Asp Phe Val Ser Leu Gln
                500                 505                 510

Val Asn Ile Asn Ser Pro Ile Thr Gln Arg Tyr Arg Leu Arg Phe Arg
            515                 520                 525

Tyr Ala Ser Ser Arg Asp Ala Arg Val Ile Val Leu Thr Gly Ala Ala
        530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
                580                 585                 590

Ile Ser Glu Gln Pro Leu Phe Gly Ala Gly Ser Ile Ser Ser Gly Glu
            595                 600                 605

Leu Tyr Ile Asp Lys Ile Glu Ile Ile Leu Ala Asp Ala Thr Phe Glu
        610                 615                 620

Ala Glu Ser Asp Leu Glu Arg Ala Gln Lys Ala Val Asn Ala Leu Phe
625                 630                 635                 640

Thr Ser Ser Asn Gln Ile Gly Leu Lys Thr Asp Val Thr Asp Tyr His
                645                 650                 655

Ile Asp Gln Val Ser Asn Leu Val Asp Cys Leu Ser Asp Glu Phe Cys
                660                 665                 670

Leu Asp Glu Lys Lys Glu Leu Ser Glu Lys Val Lys His Ala Lys Arg
            675                 680                 685

Leu Ser Asp Glu Arg Asn Leu Leu Gln Asp Pro Asn Phe Arg Gly Ile
        690                 695                 700

Asn Arg Gln Leu Asp Arg Gly Trp Arg Gly Ser Thr Asp Ile Thr Ile
705                 710                 715                 720
```

-continued

```
Gln Gly Gly Asp Asp Val Phe Lys Glu Asn Tyr Val Thr Leu Gln Gly
            725                 730                 735

Thr Phe Asp Glu Cys Tyr Pro Thr Tyr Leu Tyr Gln Pro Ile Asp Glu
        740                 745                 750

Ser Lys Leu Lys Ala Tyr Thr Arg Tyr Gln Leu Arg Gly Tyr Ile Glu
    755                 760                 765

Asp Ser Gln Asp Leu Glu Ile Tyr Leu Ile Arg Tyr Asn Ala Lys His
770                 775                 780

Glu Thr Val Asn Val Pro Gly Thr Gly Ser Leu Trp Pro Leu Ser Ala
785                 790                 795                 800

Pro Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
            820                 825                 830

Cys Ala His His Ser His His Phe Ser Leu Asp Ile Asp Val Gly Cys
        835                 840                 845

Thr Asp Leu Asn Glu Asp Leu Gly Val Trp Val Ile Phe Lys Ile Lys
    850                 855                 860

Thr Gln Asp Gly His Ala Arg Leu Gly Asn Leu Glu Phe Leu Glu Glu
865                 870                 875                 880

Lys Pro Leu Val Gly Glu Ala Leu Ala Arg Val Lys Arg Ala Glu Lys
                885                 890                 895

Lys Trp Arg Asp Lys Arg Glu Lys Leu Glu Trp Glu Thr Asn Ile Val
            900                 905                 910

Tyr Lys Glu Ala Lys Glu Ser Val Asp Ala Leu Phe Val Asn Ser Gln
        915                 920                 925

Tyr Asp Arg Leu Gln Ala Asp Thr Asn Ile Ala Met Ile His Ala Ala
    930                 935                 940

Asp Lys Arg Val His Ser Ile Arg Glu Ala Tyr Leu Pro Glu Leu Ser
945                 950                 955                 960

Val Ile Pro Gly Val Asn Ala Ala Ile Phe Glu Glu Leu Glu Gly Arg
                965                 970                 975

Ile Phe Thr Ala Phe Ser Leu Tyr Asp Ala Arg Asn Val Ile Lys Asn
            980                 985                 990

Gly Asp Phe Asn Asn Gly Leu Ser  Cys Trp Asn Val Lys  Gly His Val
        995                 1000                1005

Asp Val  Glu Glu Gln Asn  Asn His Arg Ser Val  Leu Val Val Pro
    1010                1015                1020

Glu Trp  Glu Ala Glu Val  Ser Gln Glu Val Arg  Val Cys Pro Gly
    1025                1030                1035

Arg Gly  Tyr Ile Leu Arg  Val Thr Ala Tyr Lys  Glu Gly Tyr Gly
    1040                1045                1050

Glu Gly  Cys Val Thr Ile  His Glu Ile Glu Asn  Thr Asp Glu
    1055                1060                1065

Leu Lys  Phe Ser Asn Cys  Val Glu Glu Val Tyr  Pro Asn Asn
    1070                1075                1080

Thr Val  Thr Cys Asn Asp Tyr  Thr Ala Thr Gln Glu  Glu Tyr Glu
    1085                1090                1095

Gly Thr  Tyr Thr Ser Arg Asn  Arg Gly Tyr Asp Gly  Ala Tyr Glu
    1100                1105                1110

Ser Asn  Ser Ser Val Pro  Ala  Asp Tyr Ala Ser Ala  Tyr Glu Glu
    1115                1120                1125
```

-continued

```
Lys Ala Tyr Thr Asp Gly Arg Arg Asp Asn Pro Cys Glu Ser Asn
1130                1135                1140

Arg Gly Tyr Gly Asp Tyr Thr Pro Leu Pro Ala Gly Tyr Val Thr
1145                1150                1155

Lys Glu Leu Glu Tyr Phe Pro Glu Thr Asp Lys Val Trp Ile Glu
1160                1165                1170

Ile Gly Glu Thr Glu Gly Thr Phe Ile Val Asp Ser Val Glu Leu
1175                1180                1185

Ile Ile Met Glu Glu
1190

<210> SEQ ID NO 6
<211> LENGTH: 722
<212> TYPE: PRT
<213> ORGANISM: Bacillus thuringiensis

<400> SEQUENCE: 6

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
    210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Gly Asn Phe Asp Gly Ser Phe Trp Gly Ser Ala Gln Gly Ile Glu
        275                 280                 285

Gly Ser Ile Arg Ser Pro His Leu Met Asp Ile Leu Asn Ser Ile Thr
    290                 295                 300
```

-continued

```
Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
        340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
        370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Val Ser Ile Ile
            435                 440                 445

Arg Ala Pro Met Phe Ser Trp Ile His Arg Ser Ala Glu Phe Asn Asn
    450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
            515                 520                 525

Tyr Ala Ser Thr Thr Asn Leu Gln Phe His Thr Ser Ile Asp Gly Arg
            530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
            580                 585                 590

Ser Gly Asn Glu Val Tyr Ile Asp Arg Ile Glu Phe Val Pro Ala Glu
            595                 600                 605

Val Thr Phe Glu Ala Glu Tyr Asp Leu Glu Arg Ala Gln Lys Ala Val
    610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
                660                 665                 670

His Ala Lys Arg Leu Ser Asp Glu Arg Asn Leu Leu Gln Asp Pro Asn
            675                 680                 685
```

```
Phe Arg Gly Ile Asn Arg Gln Leu Asp Arg Gly Trp Arg Gly Ser Thr
    690                 695                 700
Asp Ile Thr Ile Gln Gly Gly Asp Asp Val Phe Lys Glu Asn Tyr Val
705                 710                 715                 720
Thr Leu
```

What is claimed is:

1. A composition comprising a first monoclonal MAb58 antibody produced by a hybridoma cell line deposited as ATCC Accession No. PTA-122985 and a second monoclonal antibody H04MAb70 produced by a hybridoma cell line deposited as ATCC Accession No. PTA-122984, wherein the first and second antibody that function together to specifically detect or quantitate a Cry1A.105 protein comprising SEQ ID NO:4 in an immunoassay of a biological sample comprising the Cry1A.105 protein and a Cry1Ab protein comprising SEQ ID NO:1, wherein the first antibody and the second antibody individually are capable of binding to both the Cry1Ab protein and the Cry1A.105 protein but that function together in the immunoassay to specifically detect or quantitate the Cry1A.105 protein and not the Cry1Ab protein.

2. The composition of claim 1, wherein the immunoassay is an enzyme-linked immunosorbent assay (ELISA).

3. The composition of claim 2, wherein the first antibody is a coating antibody and the second antibody is a detecting antibody.

4. The composition of claim 3, wherein the coating antibody is MAb58 and the detecting antibody is HO4MAb70.

5. The composition of claim 1, wherein the biological sample is a transgenic plant sample.

6. The composition of claim 5, wherein the transgenic plant is a transgenic corn plant.

7. The composition of claim 6, wherein the transgenic corn plant comprises event MON89034.

8. The composition of claim 7, wherein the Cry1A.105 protein is from event MON89034 and the Cry1Ab protein is from Bt11.

9. The composition of claim 8, wherein the biological sample further comprises an eCry3A.1Ab protein from event 5307.

10. A monoclonal antibody produced by a hybridoma deposited as ATCC Accession No. PTA-122985.

11. A method for specifically detecting or quantitating a Cry1A.105 protein comprising SEQ ID NO:4 in a biological sample from a transgenic plant comprising the Cry1A.105 protein and a Cry1Ab protein comprising SEQ ID NO:1, the method comprising (a) obtaining the biological sample; (b) performing an immunoassay on the biological sample, wherein the immunoassay comprises the composition of claim 1, resulting in the specific detection or quantitation of the Cry1A.105 protein.

12. The method of claim 11, wherein the transgenic plant is a transgenic corn plant that comprises event MON89034.

13. The method of claim 12, wherein the transgenic plant further comprises event Bt11 or event 5307.

14. An immunoassay method to detect or quantitate a Cry1A.105 protein comprising SEQ ID NO:4 and a Cry1Ab protein comprising SEQ ID NO:1 in a biological sample from a transgenic corn plant comprising the Cry1Ab protein and the Cry1A.105 protein, the method comprising: (a) coating a first solid surface with a first antibody that is MAb58 produced by a hybridoma cell line deposited as ATCC Accession No. PTA-122985 that binds the Cry1A.105 protein but does not bind the Cry1Ab protein and coating a second solid surface with a second antibody that is 87AB1.1 that binds the Cry1Ab protein; (b) contacting the biological sample with the MAb58 antibody under conditions effective to allow the formation of a Cry1A.105-MAb58 antibody complex but does not allow the formation of a Cry1Ab-MAb58 antibody complex, resulting in a Cry1A.105-depleted biological sample; (c) removing the Cry1A.105-depleted biological sample and contacting the Cry1A.105-depleted biological sample with the 87AB1.1 antibody under conditions effective to allow the formation of a Cry1Ab protein-87AB1.1 antibody complex; (d) detecting or quantitating the Cry1A.105 protein complex on the first solid surface; and (e) detecting or quantitating the Cry1Ab protein on the second solid surface.

15. The method of claim 14, wherein the detecting of steps (d) or (e) is carried out using a composition comprising an antibody capable of binding to the Cry1A.105 protein and the Cry1Ab protein.

16. The method of claim 15, wherein the antibody is a monoclonal antibody that is HO4MAb70 produced by a hybridoma cell line deposited as ATCC Accession No. PTA-122984.

* * * * *